United States Patent
Lippincott et al.

(10) Patent No.: US 11,352,425 B2
(45) Date of Patent: Jun. 7, 2022

(54) ANTI-CD47 ANTIBODIES

(71) Applicant: Absos, LLC, New York, NY (US)

(72) Inventors: John Lippincott, San Diego, CA (US); Dana Duey, San Diego, CA (US); Larry Green, San Diego, CA (US)

(73) Assignee: ABSOS, LLC, New York, NY (US)

( * ) Notice: Subject to any disclaimer, the term of this patent is extended or adjusted under 35 U.S.C. 154(b) by 314 days.

(21) Appl. No.: 16/347,926

(22) PCT Filed: Nov. 8, 2017

(86) PCT No.: PCT/US2017/060657
§ 371 (c)(1),
(2) Date: May 7, 2019

(87) PCT Pub. No.: WO2018/089508
PCT Pub. Date: May 17, 2018

(65) Prior Publication Data
US 2019/0292258 A1    Sep. 26, 2019

Related U.S. Application Data

(60) Provisional application No. 62/536,267, filed on Jul. 24, 2017, provisional application No. 62/419,158, filed on Nov. 8, 2016.

(51) Int. Cl.
*C07K 16/00* (2006.01)
*C07K 16/28* (2006.01)

(52) U.S. Cl.
CPC ...... *C07K 16/2803* (2013.01); *C07K 2317/21* (2013.01); *C07K 2317/24* (2013.01); *C07K 2317/33* (2013.01); *C07K 2317/565* (2013.01); *C07K 2317/70* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 10,870,699 B2* | 12/2020 | Sato .............. A61K 45/06 |
| 2007/0179086 A1 | 8/2007 | Gliniak |
| 2011/0027286 A1 | 2/2011 | Thurston |
| 2014/0140989 A1 | 5/2014 | Eckelman |
| 2016/0257751 A1 | 9/2016 | Swanson |
| 2016/0304609 A1 | 10/2016 | Liu |

FOREIGN PATENT DOCUMENTS

| WO | WO2014087248 | 6/2014 |
| WO | WO2014123580 | 8/2014 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Liu, et al., "CD47 Blockade Triggers T Cell-Mediated Destruction of Immunogenic Tumors," Nature Medicine, 21(10):1209-1215 (2015).
Liu, et al., "Pre-Clinical Development of a Humanized Anti-CD47 Antibody With AntiCancer Therapeutic Potential," PLOS ONE, 10(9):1-23 (2015).
Zhao, et al., "CD47-signal regulatory protein-α (SIRPα) interactions form a barrier for antibody-mediated tumor cell destruction," PNAS, 108(45):18342-18347 (2011).

* cited by examiner

*Primary Examiner* — Meera Natarajan
(74) *Attorney, Agent, or Firm* — Haley Guiliano LLP; James F. Haley, Jr.; Brian M. Gummow

(57) ABSTRACT

The present invention provides anti-CD47 monoclonal antibodies and related compositions, which may be used in any of a variety of therapeutic and diagnostic methods for the treatment of cancer, ischemic-reperfusion injury, and other diseases.

15 Claims, 6 Drawing Sheets

Specification includes a Sequence Listing.

Figure 1: ELISA testing for antibody neutralization of CD47 binding to SIRP α

| Hybridoma | Functional | Cell Binding | Hemag | Phag |
|---|---|---|---|---|
| CD47-5A | Y | Y | | |
| CD47-10A | Y | Y | | |
| CD47-14A | Y | Y | | |
| CD47-85A | Y | Y | | |
| CD47-87A | Y | Y | | |
| CD47-91A | Y | Y | | |
| CD47-101A | Y | Y | | |
| CD47-102A | Y | Y | | |
| CD47-106A | Y | Y | | |
| CD47-107A | Y | Y | | |
| CD47-139A | Y | Y | | |
| CD47-144A | Y | Y | | |
| CD47-151A | Y | Y | | |
| CD47-153A | Y | Y | | |
| CD47-161A | Y | Y | | |
| CD47-164A | Y | Y | | |
| CD47-90A | Y-WEAK | Y-WEAK | | |
| CD47-143A | Y-WEAK | Y-WEAK | | |
| CD47-47A | N | Y-WEAK | | |
| CD47-141A | N | Y-WEAK | | |
| CD47-1A | N | N | | |
| CD47-2A | N | N | | |
| CD47-3A | N | N | | |
| CD47-4A | N | N | | |
| CD47-6A | N | N | | |
| CD47-7A | N | N | | |
| CD47-8A | N | N | | |
| CD47-9A | N | N | | |
| CD47-12A | N | N | | |
| CD47-13A | N | N | | |
| CD47-15A | N | N | | |
| CD47-16A | N | N | | |
| CD47-17A | N | N | | |
| CD47-19A | N | N | | |
| CD47-20A | N | N | | |
| CD47-21A | N | N | | |
| CD47-22A | N | N | | |
| CD47-24A | N | N | | |

*FIG. 2 (Continued)*

| | 84 | 163 | 165 | 24 | 34 | 34 | 157 | 133 | 142 | 4 | 17 | 107 | 101 | 161 | 5 | 85 | 17 | 5 | 6 | 4 | 17 | 107 | 101 | 154 | 158 | 164 |
|---|---|---|---|---|---|---|---|---|---|---|---|---|---|---|---|---|---|---|---|---|---|---|---|---|---|---|
| 1A | 82 | 117 | 122 | 96 | 105 | 89 | 106 | 94 | 93 | 90 | 88 | 96 | 105 | 106 | 97 | 98 | 108 | 112 | 95 | 90 | 94 | 111 | 118 | 102 | 112 | 103 |
| 27A | 95 | 117 | 95 | 100 | 113 | 102 | 114 | 103 | 95 | 103 | 108 | 106 | 104 | 105 | 107 | 98 | 95 | 113 | 105 | 108 | 115 | 106 | 126 | 96 | 103 | 108 |
| 10A | 3 | 3 | 2 | 91 | 106 | 89 | 89 | 89 | 101 | 97 | 86 | 85 | 61 | 89 | 73 | 83 | 91 | 93 | 103 | 106 | 97 | 100 | 92 | 102 | 109 | 97 |
| 35A | 75 | 115 | 95 | 111 | 111 | 91 | 105 | 106 | 98 | 110 | 103 | 102 | 101 | 109 | 97 | 104 | 88 | 73 | 109 | 116 | 107 | 105 | 119 | 99 | 104 | 117 |
| 156A | 91 | 107 | 109 | 21 | 52 | 32 | 45 | 42 | 52 | 106 | 106 | 101 | 106 | 112 | 110 | 95 | 91 | 104 | 105 | 94 | 102 | 107 | 121 | 101 | 93 | 120 |
| 141A | 78 | 75 | 59 | 114 | 110 | 97 | 104 | 100 | 100 | 99 | 105 | 92 | 94 | 107 | 102 | 102 | 92 | 100 | 115 | 103 | 103 | 101 | 100 | 90 | 99 | 100 |
| G1 Alone | 100 | 100 | 100 | 100 | 100 | 100 | 100 | 100 | 100 | 100 | 100 | 100 | 100 | 100 | 100 | 100 | 86 | 102 | 100 | 100 | 100 | 100 | 100 | 100 | 100 | 100 |

ANTI-CD47 ANTIBODIES

CROSS REFERENCE TO RELATED APPLICATIONS

This application is a United States National Phase Application filed under 35 U.S.C. § 371 from International Patent Application No. PCT/US2017/060657, filed on Nov. 8, 2017, which claims the benefit under 35 U.S.C. § 119(e) of U.S. Provisional Application No. 62/536,267, filed Jul. 24, 2017, and U.S. Provisional Application No. 62/419,158, filed Nov. 8, 2016. The contents and disclosures of each of these applications are each incorporated by reference herein in their entireties.

SEQUENCE LISTING

The Sequence Listing associated with this application is provided in text format in lieu of a paper copy, and is hereby incorporated by reference the specification. The name of the text file containing the Sequence Listing is 000118-0007-301.SL.txt. The text file was created on May 7, 2019 and is 126,347 bytes in size, and is being submitted electronically via EFS-Web.

BACKGROUND

Technical Field

The present invention relates generally to anti-CD47 antibodies, compositions and methods of using same. Such antibodies are useful, for example, for treating a variety of diseases, such as oncological and immunological diseases.

Description of the Related Art

CD47 is a five-pass integral membrane protein with a large extracellular domain of 123 amino acids. The biology of CD47 is reviewed in Murata et al., J. Biochem (2014) 155: 335-344. CD47 is a tumor antigen that prevents phagocytosis by SIRP α expressing macrophages. CD47/SIRP α blocking antibodies can induce phagocytosis of tumor cells by macrophages.

Anti-CD47 antibodies that induce phagocytosis may have utility in the treatment of cancer and inflammatory and autoimmune diseases. In particular, CD47 mAbs may be useful for treating cancer as a monotherapy or in combination therapy. Macrophages that have been induced to phagocytose cancer cells by anti-CD47 monoclonal antibodies (mAbs) further stimulate an anti-cancer response by displaying tumor antigens in the MHC to stimulate a secondary immune response against the cancer cells. The importance of macrophages in cancer therapy is reviewed in Weiskopf and Weissman, MAbs (2015) 7: 303-310. CD47 is expressed on cells in normal human tissue in humans. In particular, it is expressed on human erythrocytes (red blood cells, RBCs). Some anti-CD47 antibodies can induce hemagglutination. There is a need for therapeutic candidate CD47 mAbs that exhibit both induction of macrophage phagocytosis of cancer cells and have very low to no hemagglutination at high concentrations.

SUMMARY OF THE INVENTION

The present invention relates to anti-CD47 antibodies. More specifically, it relates to chimeric anti-CD47 antibodies generated from an AlivaMab Mouse, fully human anti-CD47 antibodies produced therefrom, and methods of use thereof.

One aspect of the invention provides an isolated anti-CD47 antibody, or an antigen-binding fragment thereof, comprising i) a heavy chain variable region comprising a VHCDR1 disclosed herein, a VHCDR2 disclosed herein, and a VHCDR3 disclosed herein and ii) a light chain variable region comprising a VLCDR1 disclosed herein, a VLCDR2 disclosed herein, and a VLCDR3 disclosed herein.

In one embodiment, the anti-CD47 antibody, or antigen-binding fragment thereof, comprises the VHCDR1 of SEQ ID NO:22, the VHCDR2 of SEQ ID NO:43, the VHCDR3 of SEQ ID NO:64, the VLCDR1 of SEQ ID NO:106, the VLCDR2 of SEQ ID NO:127, and the VLCDR3 of SEQ ID NO:148.

In one embodiment, the anti-CD47 antibody, or antigen-binding fragment thereof, comprises the VHCDR1 of SEQ ID NO:23, the VHCDR2 of SEQ ID NO:44, the VHCDR3 of SEQ ID NO:65, the VLCDR1 of SEQ ID NO:107, the VLCDR2 of SEQ ID NO:128, and the VLCDR3 of SEQ ID NO:149.

In one embodiment, the anti-CD47 antibody, or antigen-binding fragment thereof, comprises the VHCDR1 of SEQ ID NO:24, the VHCDR2 of SEQ ID NO:45, the VHCDR3 of SEQ ID NO:66, the VLCDR1 of SEQ ID NO:108, the VLCDR2 of SEQ ID NO:129, and the VLCDR3 of SEQ ID NO:150.

In one embodiment, the anti-CD47 antibody, or antigen-binding fragment thereof, comprises the VHCDR1 of SEQ ID NO:25, the VHCDR2 of SEQ ID NO:46, the VHCDR3 of SEQ ID NO:67, the VLCDR1 of SEQ ID NO:109, the VLCDR2 of SEQ ID NO:130, and the VLCDR3 of SEQ ID NO:151.

In one embodiment, the anti-CD47 antibody, or antigen-binding fragment thereof, comprises the VHCDR1 of SEQ ID NO:26, the VHCDR2 of SEQ ID NO:47, the VHCDR3 of SEQ ID NO:68, the VLCDR1 of SEQ ID NO:110, the VLCDR2 of SEQ ID NO:131, and the VLCDR3 of SEQ ID NO:152.

In one embodiment, the anti-CD47 antibody, or antigen-binding fragment thereof, comprises the VHCDR1 of SEQ ID NO:27, the VHCDR2 of SEQ ID NO:48, the VHCDR3 of SEQ ID NO:69, the VLCDR1 of SEQ ID NO:111, the VLCDR2 of SEQ ID NO:132, and the VLCDR3 of SEQ ID NO:153.

In one embodiment, the anti-CD47 antibody, or antigen-binding fragment thereof, comprises the VHCDR1 of SEQ ID NO:28, the VHCDR2 of SEQ ID NO:49, the VHCDR3 of SEQ ID NO:70, the VLCDR1 of SEQ ID NO:112, the VLCDR2 of SEQ ID NO:133, and the VLCDR3 of SEQ ID NO:154.

In one embodiment, the anti-CD47 antibody, or antigen-binding fragment thereof, comprises the VHCDR1 of SEQ ID NO:29, the VHCDR2 of SEQ ID NO:50, the VHCDR3 of SEQ ID NO:71, the VLCDR1 of SEQ ID NO:113, the VLCDR2 of SEQ ID NO:134, and the VLCDR3 of SEQ ID NO:155.

In one embodiment, the anti-CD47 antibody, or antigen-binding fragment thereof, comprises the VHCDR1 of SEQ ID NO:30, the VHCDR2 of SEQ ID NO:51, the VHCDR3 of SEQ ID NO:72, the VLCDR1 of SEQ ID NO:114, the VLCDR2 of SEQ ID NO:135, and the VLCDR3 of SEQ ID NO:156.

In one embodiment, the anti-CD47 antibody, or antigen-binding fragment thereof, comprises the VHCDR1 of SEQ ID NO:31, the VHCDR2 of SEQ ID NO:52, the VHCDR3 of SEQ ID NO:73, the VLCDR1 of SEQ ID NO:115, the VLCDR2 of SEQ ID NO:136, and the VLCDR3 of SEQ ID NO:157.

In one embodiment, the anti-CD47 antibody, or antigen-binding fragment thereof, comprises the VHCDR1 of SEQ ID NO:32, the VHCDR2 of SEQ ID NO:53, the VHCDR3 of SEQ ID NO:74, the VLCDR1 of SEQ ID NO:116, the VLCDR2 of SEQ ID NO:137, and the VLCDR3 of SEQ ID NO:158.

In one embodiment, the anti-CD47 antibody, or antigen-binding fragment thereof, comprises the VHCDR1 of SEQ ID NO:33, the VHCDR2 of SEQ ID NO:54, the VHCDR3 of SEQ ID NO:75, the VLCDR1 of SEQ ID NO:117, the VLCDR2 of SEQ ID NO:138, and the VLCDR3 of SEQ ID NO:159.

In one embodiment, the anti-CD47 antibody, or antigen-binding fragment thereof, comprises the VHCDR1 of SEQ ID NO:34, the VHCDR2 of SEQ ID NO:55, the VHCDR3 of SEQ ID NO:76, the VLCDR1 of SEQ ID NO:118, the VLCDR2 of SEQ ID NO:139, and the VLCDR3 of SEQ ID NO:160.

In one embodiment, the anti-CD47 antibody, or antigen-binding fragment thereof, comprises the VHCDR1 of SEQ ID NO:35, the VHCDR2 of SEQ ID NO:56, the VHCDR3 of SEQ ID NO:77, the VLCDR1 of SEQ ID NO:119, the VLCDR2 of SEQ ID NO:140, and the VLCDR3 of SEQ ID NO:161.

In one embodiment, the anti-CD47 antibody, or antigen-binding fragment thereof, comprises the VHCDR1 of SEQ ID NO:36, the VHCDR2 of SEQ ID NO:57, the VHCDR3 of SEQ ID NO:78, the VLCDR1 of SEQ ID NO:120, the VLCDR2 of SEQ ID NO:141, and the VLCDR3 of SEQ ID NO:162.

In one embodiment, the anti-CD47 antibody, or antigen-binding fragment thereof, comprises the VHCDR1 of SEQ ID NO:37, the VHCDR2 of SEQ ID NO:58, the VHCDR3 of SEQ ID NO:79, the VLCDR1 of SEQ ID NO:121, the VLCDR2 of SEQ ID NO:142, and the VLCDR3 of SEQ ID NO:163.

In one embodiment, the anti-CD47 antibody, or antigen-binding fragment thereof, comprises the VHCDR1 of SEQ ID NO:38, the VHCDR2 of SEQ ID NO:59, the VHCDR3 of SEQ ID NO:80, the VLCDR1 of SEQ ID NO:122, the VLCDR2 of SEQ ID NO:143, and the VLCDR3 of SEQ ID NO:164.

In one embodiment, the anti-CD47 antibody, or antigen-binding fragment thereof, comprises the VHCDR1 of SEQ ID NO:39, the VHCDR2 of SEQ ID NO:60, the VHCDR3 of SEQ ID NO:81, the VLCDR1 of SEQ ID NO:123, the VLCDR2 of SEQ ID NO:144, and the VLCDR3 of SEQ ID NO:165.

In one embodiment, the anti-CD47 antibody, or antigen-binding fragment thereof, comprises the VHCDR1 of SEQ ID NO:40, the VHCDR2 of SEQ ID NO:61, the VHCDR3 of SEQ ID NO:82, the VLCDR1 of SEQ ID NO:124, the VLCDR2 of SEQ ID NO:145, and the VLCDR3 of SEQ ID NO:166.

In one embodiment, the anti-CD47 antibody, or antigen-binding fragment thereof, comprises the VHCDR1 of SEQ ID NO:41, the VHCDR2 of SEQ ID NO:62, the VHCDR3 of SEQ ID NO:83, the VLCDR1 of SEQ ID NO:125, the VLCDR2 of SEQ ID NO:146, and the VLCDR3 of SEQ ID NO:167.

In one embodiment, the anti-CD47 antibody, or antigen-binding fragment thereof, comprises the VHCDR1 of SEQ ID NO:42, the VHCDR2 of SEQ ID NO:63, the VHCDR3 of SEQ ID NO:84, the VLCDR1 of SEQ ID NO:126, the VLCDR2 of SEQ ID NO:147, and the VLCDR3 of SEQ ID NO:168.

In one embodiment, the VH comprises an amino acid sequence of one of SEQ ID NOs:1-21. In another embodiment, the VL comprises an amino acid sequence of one of SEQ ID NOs:85-105. In another embodiment, the VH comprises an amino acid sequence of one of SEQ ID NOs:1-21, and the VL comprises an amino acid sequence of one of SEQ ID NOs:85-105. In one embodiment, the VH and the VL are from the same anti-CD47 AlivaMab Antibody.

In one embodiment, the anti-CD47 antibody, or antigen-binding fragment thereof, is human. In one embodiment, the antibody is chimeric. In certain embodiments, the antibody is selected from a single-variable domain antibody, single chain antibody, a scFv, a bispecific antibody, a multi-specific antibody, a Fab, a F(ab')2, and a whole antibody.

One aspect of the invention provides a recombinant polynucleotide encoding the anti-CD47 antibody, or antigen-binding fragment thereof, described above. Another aspect of the invention provides an expression vector comprising the recombinant polynucleotide. In another aspect of the invention provides an isolated host cell that comprises the expression vector. One aspect of the invention provides a composition comprising an anti-CD47 antibody, or antigen-binding fragment thereof, described herein and a physiologically acceptable carrier.

BRIEF DESCRIPTION OF THE FIGURES

FIG. 5 shows the epitope binning of anti-CD47 mAbs.

BRIEF DESCRIPTION OF THE SEQUENCES

TABLE 1

Figure 1:
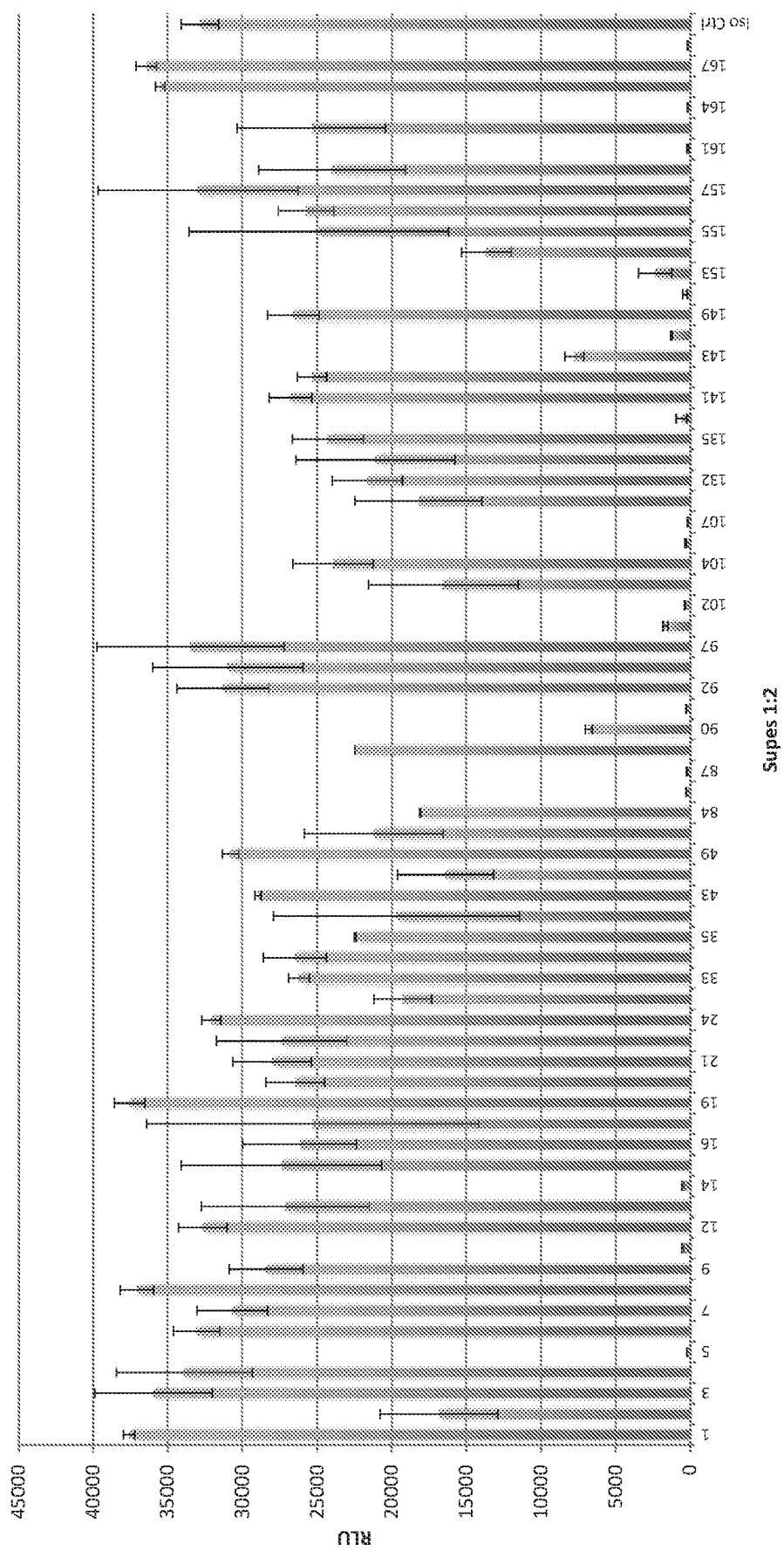
FIG. 1 shows that 16 of the 61 antibodies tested substantially or completely blocked binding of human CD47 to SIRP α.

| Anti-CD47 AlivaMab Antibody Amino Acid Sequences | | | | | | | | |
|---|---|---|---|---|---|---|---|---|
| Clone | VH (V-D-J) SEQ ID NO | VHCDR1 SEQ ID NO | VHCDR2 SEQ ID NO | VHCDR3 SEQ ID NO | VL (V-J) SEQ ID NO | VLCDR1 SEQ ID NO | VLCDR2 SEQ ID NO | VLCDR3 SEQ ID NO |
| 5 | 1 | 22 | 43 | 64 | 85 | 106 | 127 | 148 |
| 10 | 2 | 23 | 44 | 65 | 86 | 107 | 128 | 149 |

TABLE 1-continued

Anti-CD47 AlivaMab Antibody Amino Acid Sequences

| Clone | VH (V-D-J) SEQ ID NO | VHCDR1 SEQ ID NO | VHCDR2 SEQ ID NO | VHCDR3 SEQ ID NO | VL (V-J) SEQ ID NO | VLCDR1 SEQ ID NO | VLCDR2 SEQ ID NO | VLCDR3 SEQ ID NO |
|---|---|---|---|---|---|---|---|---|
| 14 | 3 | 24 | 45 | 66 | 87 | 108 | 129 | 150 |
| 85 | 4 | 25 | 46 | 67 | 88 | 109 | 130 | 151 |
| 87 | 5 | 26 | 47 | 68 | 89 | 110 | 131 | 152 |
| 90 | 6 | 27 | 48 | 69 | 90 | 111 | 132 | 153 |
| 91 | 7 | 28 | 49 | 70 | 91 | 112 | 133 | 154 |
| 101 | 8 | 29 | 50 | 71 | 92 | 113 | 134 | 155 |
| 102 | 9 | 30 | 51 | 72 | 93 | 114 | 135 | 156 |
| 106 | 10 | 31 | 52 | 73 | 94 | 115 | 136 | 157 |
| 107 | 11 | 32 | 53 | 74 | 95 | 116 | 137 | 158 |
| 139 | 12 | 33 | 54 | 75 | 96 | 117 | 138 | 159 |
| 143 | 13 | 34 | 55 | 76 | 97 | 118 | 139 | 160 |
| 144 | 14 | 35 | 56 | 77 | 98 | 119 | 140 | 161 |
| 151 | 15 | 36 | 57 | 78 | 99 | 120 | 141 | 162 |
| 153 | 16 | 37 | 58 | 79 | 100 | 121 | 142 | 163 |
| 161 | 17 | 38 | 59 | 80 | 101 | 122 | 143 | 164 |
| 164 | 18 | 39 | 60 | 81 | 102 | 123 | 144 | 165 |
| 201 | 19 | 40 | 61 | 82 | 103 | 124 | 145 | 166 |
| 204 | 20 | 41 | 62 | 83 | 104 | 125 | 146 | 167 |
| 205 | 21 | 42 | 63 | 84 | 105 | 126 | 147 | 168 |

TABLE 2

Anti-CD47 AlivaMab Antibody Polynucleotide Sequences

| Clone | VH SEQ ID NO | VHCDR1 SEQ ID NO | VHCDR2 SEQ ID NO | VHCDR3 SEQ ID NO | VL SEQ ID NO | VLCDR1 SEQ ID NO | VLCDR2 SEQ ID NO | VLCDR3 SEQ ID NO |
|---|---|---|---|---|---|---|---|---|
| 5 | 169 | 190 | 211 | 232 | 253 | 274 | 295 | 316 |
| 10 | 170 | 191 | 212 | 233 | 254 | 275 | 296 | 317 |
| 14 | 171 | 192 | 213 | 234 | 255 | 276 | 297 | 318 |
| 85 | 172 | 193 | 214 | 235 | 256 | 277 | 298 | 319 |
| 87 | 173 | 194 | 215 | 236 | 257 | 278 | 299 | 320 |
| 90 | 174 | 195 | 216 | 237 | 258 | 279 | 300 | 321 |
| 91 | 175 | 196 | 217 | 238 | 259 | 280 | 301 | 322 |
| 101 | 176 | 197 | 218 | 239 | 260 | 281 | 302 | 323 |
| 102 | 177 | 198 | 219 | 240 | 261 | 282 | 303 | 324 |
| 106 | 178 | 199 | 220 | 241 | 262 | 283 | 304 | 325 |
| 107 | 179 | 200 | 221 | 242 | 263 | 284 | 305 | 326 |
| 139 | 180 | 201 | 222 | 243 | 264 | 285 | 306 | 327 |
| 143 | 181 | 202 | 223 | 244 | 265 | 286 | 307 | 328 |
| 144 | 182 | 203 | 224 | 245 | 266 | 287 | 308 | 329 |
| 151 | 183 | 204 | 225 | 246 | 267 | 288 | 309 | 330 |
| 153 | 184 | 205 | 226 | 247 | 268 | 289 | 310 | 331 |
| 161 | 185 | 206 | 227 | 248 | 269 | 290 | 311 | 332 |
| 164 | 186 | 207 | 228 | 249 | 270 | 291 | 312 | 333 |
| 201 | 187 | 208 | 229 | 250 | 271 | 292 | 313 | 334 |
| 204 | 188 | 209 | 230 | 251 | 272 | 293 | 314 | 335 |
| 205 | 189 | 210 | 231 | 252 | 273 | 294 | 315 | 336 |

SEQ ID NO:337 is a 3' IgG-specific primer.
SEQ ID NO:338 is a 3' Igκ-specific primer.

DETAILED DESCRIPTION

The present disclosure relates to anti-CD47 antibodies. Ablexis has used its proprietary AlivaMab Mouse technology (See WO 2010/039900 and WO 2011/123708, incorporated herein in their entirety) to generate panels of monoclonal antibodies (mAbs) against human CD47. Antibodies that potently neutralize SIRPα binding to CD47 were identified within the panel of anti-CD47 AlivaMab antibodies. In one embodiment, anti-CD47 AlivaMab antibodies potently induce phagocytosis of tumor cells by macrophages. In one embodiment, anti-CD47 AlivaMab antibodies that do not induce hemagglutination of erythrocytes, even at high concentration, were identified.

Embodiments of the invention pertain to the use of anti-CD47 antibodies, or antigen-binding fragments thereof, for the diagnosis, assessment and treatment of diseases and disorders associated with CD47 or aberrant expression thereof. The subject antibodies are used in the treatment or prevention of neoplasms, among other diseases. The subject antibodies may also be used in the blocking of ischemia-reperfusion injury.

Portions of variable regions from the AlivaMab antibodies may include all or a combination of the complementarity determining regions (CDRs) of the VH and/or VL. The variable regions may be formatted with constant regions, either native or desirably modified for induction of either up-regulation or down-regulation of various effector functions, in a standard antibody structure (two heavy chains with two light chains). The variable regions may also be formatted as multi-specific antibodies, e.g., bispecific antibodies binding to two different epitopes on CD47 or to two different antigens, one of which is CD47. The variable regions may also be formatted as antibody fragments, e.g., single-domain antibodies comprising a single VH or VL, Fab, Fab'2, or chimeric antigen receptor (CAR). The antibodies may also be used as antibody-drug conjugates, or carry other additions such as small molecule toxins, biologic toxins, cytokines, oligopeptides, RNAs, or CAR-T cells to increase therapeutic modality and/or increase safety.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al., Short Protocols in Molecular Biology, 3rd ed., Wiley & Sons, 1995; Sambrook and Russell, Molecular Cloning: A Laboratory Manual (3rd Edition, 2001); Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

Before describing certain embodiments in detail, it is to be understood that this invention is not limited to particular compositions or biological systems, which can vary. It is also to be understood that the terminology used herein is for the purpose of describing particular illustrative embodiments only, and is not intended to be limiting. The terms used in this specification generally have their ordinary meaning in the art, within the context of this invention and in the specific context where each term is used. Certain terms are discussed below or elsewhere in the specification, to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

The terms "antibody" and "immunoglobulin" (Ig) are used interchangeably herein. An antibody may be either membrane bound or secreted. As used herein, the term encompasses not only intact, or "whole", polyclonal or monoclonal antibodies, but also fragments thereof (such as single-variable domain (VH, VL or combination thereof) antibodies, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, chimeric antigen receptors (CARs), and any other modified configuration of the immunoglobulin molecule that comprises an antigen-binding site or fragment (epitope recognition site) of the required specificity.

Antibody, or Ig, molecules are typically comprised of two identical heavy chains and two identical light chains linked together through disulfide bonds. Both heavy chains (IgH) and light chains (IgL) contain a variable (V) region or domain and a constant (C) region or domain. The portion of the IgH locus encoding the V region comprises multiple copies of variable (V), diversity (D), and joining (J) gene segments. The portion of the IgL loci encoding the V region comprises multiple copies of V and J gene segments. The V region encoding portion of the IgH and IgL loci undergo gene segment rearrangement, e.g., different combinations of a V, (D) and J gene segments arrange to form the IgH and IgL variable regions, to develop diverse antigen specificity in antibodies. Each variable region comprises three complementarity-determining regions (CDRs) interspersed between the less variable framework regions (FRs). The heavy chain comprises VHCDR1, VHCDR2, and VHCDR3. The light chain comprises VLCDR1, VLCDR2, and VLCDR3. The secreted form of the IgH C region is made up of three C domains, CH1, CH2, CH3, optionally CH4 (Cμ), and a hinge region except for Cμ, which lacks a hinge region. The membrane-bound form of the IgH C region also has membrane and intra-cellular domains. The IgH constant region determines the isotype of the antibody, e.g. IgM, IgD, IgG1, IgG2, IgG3, IgG4, IgA and IgE. It will be appreciated that non-human mammals, such as an AlivaMab Mouse, encoding multiple Ig isotypes will be able to undergo isotype class switching. There are two types of human IgL, Igκ and Igλ.

The term "antigen-binding fragment" as used herein refers to a polypeptide fragment that contains at least one CDR of an immunoglobulin heavy and/or light chain that binds to CD47. In this regard, an antigen-binding fragment of the antibodies may comprise 1, 2, 3, 4, 5, or all 6 CDRs of a VH and VL sequence set forth herein from anti-CD47 antibodies described herein. An antigen-binding fragment of the CD47-specific antibodies described herein is capable of binding to CD47. In certain embodiments, an antigen-binding fragment or an antibody comprising an antigen-binding fragment, prevents or inhibits SIRPα binding to CD47 and subsequent signaling events. In certain embodiments, the antigen-binding fragment binds specifically to and/or inhibits or modulates the biological activity of human CD47.

In certain embodiments, antibodies and antigen-binding fragments thereof as described herein include a heavy chain and a light chain CDR set, respectively interposed between a heavy chain and a light chain framework region (FR) set that provide conformational support to the CDRs and define the spatial relationship of the CDRs relative to each other. As used herein, the term "CDR set" refers to the three hypervariable regions of a heavy or light chain V region. Proceeding from the N terminus of a heavy or light chain, these regions are denoted as "CDR1," "CDR2," and "CDR3" respectively. An antigen-binding site, therefore, includes six CDRs, comprising the CDR set from each of a heavy and a light chain V region.

A "Fab" domain or fragment comprises the N-terminal portion of the IgH, which includes the V region and the CH1 domain of the IgH, and the entire IgL. A "F(ab')$_2$" domain comprises the Fab domain and a portion of the hinge region, wherein the 2 IgH are linked together via disulfide linkage in the middle hinge region. Both the Fab and F(ab')$_2$ are "antigen-binding fragments." The C-terminal portion of the IgH, comprising the CH2 and CH3 domains, is the "Fc" domain. The Fc domain is the portion of the Ig recognized by cell receptors, such as the FcR, and to which the complement-activating protein, C1q, binds. The lower hinge region, which is encoded in the 5' portion of the CH2 exon, provides flexibility within the antibody for binding to FcR receptors. An "Fv" fragment includes a non-covalent VH:: VL heterodimer including an antigen-binding site. In certain embodiments, single chain Fv (scFv) antibodies are contemplated. A scFv is a covalently linked VH::VL heterodimer which is expressed from a gene fusion including VH- and VL-encoding genes linked by a peptide-encoding linker (Huston et al. (1988) Proc. Nat. Acad. Sci. USA 85(16): 5879-5883).

Where bispecific antibodies are to be used, these may be conventional bispecific antibodies, which can be manufactured in a variety of ways (Holliger, P. and Winter G. Current Opinion Biotechnol. 4, 446-449 (1993)), e.g., prepared chemically or from hybrid hybridomas, or may be any of the bispecific antibody fragments mentioned above.

As used herein "chimeric antibody" refers to an antibody encoded by a polynucleotide sequence containing polynucleotide sequences from two or more species, e.g., human and mouse.

As used herein "chimeric Ig chain" refers to an Ig heavy chain or an Ig light chain encoded by a polynucleotide sequence containing polynucleotide sequences from two or more species, e.g., human and mouse. For example, a chimeric Ig heavy chain may comprise a human VH domain, DH domain, JH domain, CH1 domain, and upper hinge region and mouse CH2 and CH3 domains. In one embodiment, the middle hinge region is mouse. In one embodiment, the middle hinge region is human. In one embodiment, the middle hinge region is chimeric.

"Polypeptide," "peptide" or "protein" are used interchangeably herein to describe a chain of amino acids that are linked together by chemical bonds. A polypeptide or protein may be an IgH, IgL, V domain, C domain, or an antibody.

The strength, or affinity of immunological binding interactions can be expressed in terms of the dissociation constant ($K_D$) of the interaction, wherein a smaller $K_D$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant, $K_D$. See, generally, Davies et al. (1990) Annual Rev. Biochem. 59:439-473.

"Polynucleotide" refers to a chain of nucleic acids that are linked together by chemical bonds. Polynucleotides include, but are not limited to, DNA, cDNA, RNA, mRNA, and gene sequences and segments. Polynucleotides may be isolated from a living source such as a eukaryotic cell, prokaryotic cell or virus, or may be derived through in vitro manipulation by using standard techniques of molecular biology, or by DNA synthesis, or by a combination of a number of techniques.

As used herein, the term "vector" refers to a nucleic acid molecule into which another nucleic acid fragment can be integrated without loss of the vector's ability to replicate. Vectors may originate from a virus, a plasmid or the cell of a higher organism. Vectors are utilized to introduce foreign or recombinant DNA into a host cell, wherein the vector is replicated.

A polynucleotide agent can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for expressing the polynucleotide and, where the polynucleotide encodes an RNA, for expressing the encoded RNA in a particular cell, either for subsequent translation of the RNA into a polypeptide or for subsequent trans regulatory activity by the RNA in the cell. An expression vector can contain the expression elements necessary to achieve, for example, sustained transcription of the encoding polynucleotide, or the regulatory elements can be operatively linked to the polynucleotide prior to its being cloned into the vector.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, alpha virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb 25:37-42, 1993; Kirshenbaum et al., J. Clin. Invest 92:381-387, 1993; each of which is incorporated herein by reference).

The term "construct" as used herein refers to a sequence of DNA artificially constructed by genetic engineering, recombineering or synthesis. In one embodiment, the DNA constructs are linearized prior to recombination. In another embodiment, the DNA constructs are not linearized prior to recombination.

The terms "inhibit", "neutralize", and "antagonize" are used interchangeably herein and encompass anti-CD47 antibodies that block, inhibit, and/or decrease the activity of CD47. Examples of CD47 activity include ligand binding, e.g., binding to SIRPα.

The term "treating" with regard to a subject, refers to improving at least one symptom of the subject's disease or disorder. Treating includes curing, improving, or at least partially ameliorating the disease or disorder.

As used herein, the term "disorder" refers to, and is used interchangeably with, the terms disease, condition, or illness.

The term "pharmaceutically acceptable carrier" refers generally to any material (e.g., carrier, excipient, or stabilizer) that may accompany a therapeutic agent and is non-toxic to the subject or patient being exposed thereto.

The term "administering," as used herein, refers to any mode of transferring, delivering, introducing, or transporting a pharmaceutical composition or other agent, such as an anti-CD47 antibody, to a subject. Such modes include oral administration, topical contact, intravenous, intraperitoneal, intramuscular, intranasal, or subcutaneous administration.

The term "inhibit" or "neutralize" or "block" may relate generally to the ability of one or more anti-CD47 antibodies of the invention to decrease a biological activity of CD47, such as intracellular signaling and/or ligand binding. The inhibition/blocking of SIRPα to CD47 preferably reduces or alters the normal level or type of cell signaling that occurs when SIRPα binds to CD47 without inhibition or blocking. Inhibition and blocking are also intended to include any measurable decrease in the binding of SIRPα to CD47 when in contact with an anti CD47 antibody as disclosed herein as compared to the ligand not in contact with an anti CD47 antibody, e.g., the blocking of SIRPα to CD47 by at least about a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease, including all integers in between. In one embodiment, a neutralizing anti-CD47 antibody inhibits binding of SIRPα to CD47 by at least about a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% decrease, including all integers in between.

An antibody, or antigen-binding fragment thereof, is said to "specifically bind," "immunologically bind," and/or is "immunologically reactive" to CD47 if it reacts at a detectable level (within, for example, an ELISA assay) with CD47, and does not react detectably with unrelated polypeptides under similar conditions. Antibodies are considered to specifically bind to a target polypeptide when the binding affinity is at least $1\times10^{-7}$ M or, preferably, at least $1\times10^{-8}$ M. In one embodiment, the antibody, or antigen-binding fragment thereof, specifically binds human CD47.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

CD47

CD47, or integrin associated protein (IAP) is expressed by a variety of cells, including, e.g., erythrocytes, and it is plays a role in a variety of cellular processes. Over-expression of CD47 is associated with proliferative diseases and disorders (e.g., neoplasms, tumors and metastases). CD47 is up-regulated in ischemia-reperfusion injury (IRI), and CD47 knock-out mice are projected in models of IRI. Thus, CD47 is an important therapeutic target for both proliferative diseases and disorders and transplants.

Anti-CD47 Antibodies

AlivaMab Mouse anti-CD47 antibodies were generated using both AlivaMab Mouse Kappa mice and AlivaMab Mouse Lambda mice (also referred to herein interchangeably as AlivaMab Kappa Mice and AlivaMab Lambda Mice, respectively). Antibodies produced by AlivaMab Kappa Mice comprise a chimeric immunoglobulin heavy (IgH) chain and a human immunoglobulin kappa (Igκ) light chain. Antibodies produced by AlivaMab Lambda Mice comprise a chimeric IgH chain and a human immunoglobulin lambda (Igλ) light chain. The chimeric IgH chain of the AlivaMab Mouse antibodies comprises a human variable region comprising a human variable heavy (VH) domain, a human diversity heavy (DH) domain, and a human joining heavy (JH) domain, a human constant heavy 1 (CH1) domain, a human upper hinge region (except for Cμ, which is naturally missing an upper hinge region), a mouse middle hinge region, a mouse CH2 domain, and a mouse CH3 domain. Upon identification of a lead candidate antibody, e.g., an anti-CD47 antibody, the human heavy chain variable region is readily appended to a fully human constant region while maintaining the antigen-binding characteristics of the parent chimeric antibody that were developed in vivo in the AlivaMab Mouse. In one embodiment, the human heavy chain variable region, CH1 and, optionally, upper hinge region of the chimeric antibody are appended to human hinge, a human CH2 domain and a human CH3 domain in order to produce a fully human antibody.

Accordingly, in one embodiment, an anti-CD47 antibody, or an antigen-binding fragment thereof, of the invention is chimeric. In one embodiment, the chimeric anti-CD47 antibody, or an antigen-binding fragment thereof, comprises a chimeric IgH chain and a human Igκ chain. In one embodiment, the chimeric anti-CD47 antibody, or an antigen-binding fragment thereof, comprises a chimeric IgH chain and a human Igλ chain. In one embodiment, the chimeric anti-CD47 antibody is human and mouse. In one embodiment, an anti-CD47 antibody, or an antigen-binding fragment thereof, of the invention is human. In one embodiment, the human anti-CD47 antibody, or an antigen-binding fragment thereof, comprises a human IgH chain and a human Igκ chain. In one embodiment, the human anti-CD47 antibody, or an antigen-binding fragment thereof, comprises a human IgH chain and a human Igλ chain. In one embodiment, the isotype of the anti-CD47 antibody is selected from IgM, IgD, IgG1, IgG2, IgG3, IgG4, IgA and IgE. In one embodiment, the isotype of the anti-CD47 antibody is selected from IgG1, IgG2, IgG3, and IgG4.

In one embodiment, the anti-CD47 antibody binds an Fc receptor (FcR) selected from an FcγR, an FcεR, and an FcαR. In one embodiment, the anti-CD47 antibody binds an FcγR selected from FcγRI (CD64), FcγRII (CD32), and FcγRIII (CD16), including isoforms thereof. In one embodiment, the Fc region of the anti-CD47 antibody comprises a mutation so that it preferentially binds a particular FcγR (see, e.g., U.S. Pat. No. 6,737,056 and U.S. 2015/0031862).

In one aspect of the invention, the CDRs of an anti-CD47 antibody, or antigen-binding fragment thereof, may be mixed and matched between the CDRs of antibody clones described herein. In one embodiment, an anti-CD47 antibody, or antigen-binding fragment thereof, comprises a VHCDR1 comprising any VHCDR1 sequence disclosed herein, a VHCDR2 comprising any VHCDR2 sequence disclosed herein, and a VHCDR3 comprising any VHCDR3 sequence disclosed herein. In one embodiment, the VHCDR1, VHCDR2 and VHCDR3 are selected from three different anti-CD47 clones disclosed herein. In one embodiment, the VHCDR1, VHCDR2 and VHCDR3 are selected from two different anti-CD47 clones disclosed herein.

In one embodiment, an anti-CD47 antibody, or an antigen-binding fragment thereof, comprises a VLCDR1 comprising any VLCDR1 sequence disclosed herein, a VLCDR2 comprising any VLCDR2 sequence disclosed herein, and a VLCDR3 comprising any VLCDR3 sequence disclosed herein. In one embodiment, the VLCDR1, VLCDR2 and VLCDR3 are selected from three different anti-CD47 clones disclosed herein. In one embodiment, the VLCDR1, VLCDR2 and VLCDR3 are selected from two different anti-CD47 clones disclosed herein.

In one aspect of the invention, the CDRs of an anti-CD47 antibody, or antigen-binding fragment thereof, are from the same anti-CD47 antibody clone disclosed herein. In one embodiment, an anti-CD47 antibody, or an antigen-binding fragment thereof, comprises a VHCDR1, a VHCDR2 and a VHCDR3 from the same anti-CD47 clone disclosed herein. In one embodiment, an anti-CD47 antibody, or an antigen-binding fragment thereof, comprises a VHCDR1, a VHCDR2, and a VHCDR3 comprising the corresponding sequences disclosed herein.

In another aspect of the invention, the CDRs of an anti-CD47 antibody, or antigen-binding fragment thereof, are selected from the corresponding VH and VL of a single clone described herein. In one embodiment, an anti-CD47 antibody, or an antigen-binding fragment thereof, comprises 1) a VHCDR1, a VHCDR2, and a VHCDR3 selected from the VHCDR1, VHCDR2 and VHCDR3 of one VH selected from any one of the VH regions disclosed herein and 2) a VLCDR1, a VLCDR2, and a VLCDR3 selected from the VLCDR1, VLCDR2 and VLCDR3 of one VL selected from any one of the VL regions disclosed herein. In one embodiment, an anti-CD47 antibody, or antigen-binding fragment thereof, comprises a VHCDR1, a VHCDR2, a VHCDR3, a VLCDR1, a VLCDR2, and a VLCDR3 within the corresponding VH and VL amino acid sequences of a single clone as disclosed herein.

In one embodiment, an anti-CD47 antibody, or antigen-binding fragment thereof, comprises a VH comprising any one of the VH regions disclosed herein. In one embodiment, an anti-CD47 antibody, or antigen-binding fragment thereof, comprises a VL comprising any one of the VL regions disclosed herein. In one embodiment, an anti-CD47 antibody, or an antigen-binding fragment thereof, comprises a corresponding VH and VL of a single clone.

In one embodiment, an anti-CD47 antibody is a whole antibody. In one embodiment, an anti-CD47 antibody is a single chain antibody. In one embodiment, an anti-CD47 antibody is a scFv. In one embodiment, an anti-CD47 antibody is a Fab. In one embodiment, an anti-CD47 antibody is a F(ab')$_2$. In one embodiment, an anti-CD47 antibody is a Fv.

In one embodiment, an anti-CD47 antibody is a bispecific antibody. In one embodiment, a bispecific anti-CD47 antibody specifically recognizes two different epitopes of CD47. In one embodiment, a bispecific anti-CD47 comprises a first CDR set comprising the VHCDR1, VHCDR2, VHCDR3, VLCDR1, VLCDR2, and VLCDR3 from a first anti-CD47 antibody clone disclosed herein and a second CDR set comprising the VHCDR1, VHCDR2, VHCDR3, VLCDR1, VLCDR2, and VLCDR3 of a second anti-CD47 antibody clone disclosed herein. In one embodiment, a bispecific anti-CD47 comprises a corresponding first VH and first VL of a first anti-CD47 antibody clone disclosed herein and a corresponding second VH and second VL of a second anti-CD47 antibody clone disclosed herein. In one embodiment, a bispecific anti-CD47 antibody specifically recognizes CD47 and another antigen.

Polynucleotides

One aspect of the present invention provides a polynucleotide sequence that encodes an anti-CD47 antibody, or antigen-binding fragment thereof, disclosed herein. In one embodiment, the polynucleotide is a recombinant polynucleotide. In one embodiment, the polynucleotide is cDNA.

In one embodiment, a polynucleotide sequence encodes a CDR of an anti-CD47 antibody disclosed herein. In one embodiment, the polynucleotide comprises a VHCDR1 polynucleotide sequence disclosed herein. In one embodiment, the polynucleotide comprises a VHCDR2 polynucleotide sequence disclosed herein. In one embodiment, the polynucleotide comprises a VHCDR3 polynucleotide sequence disclosed herein. In one embodiment, the polynucleotide comprises a VLCDR1 polynucleotide sequence disclosed herein. In one embodiment, the polynucleotide comprises a VLCDR2 polynucleotide sequence disclosed herein. In one embodiment, the polynucleotide comprises a VLCDR3 polynucleotide sequence disclosed herein.

In one embodiment, a polynucleotide sequence encodes a VH of an anti-CD47 antibody disclosed herein. In one embodiment, a polynucleotide sequence encodes a VL of an anti-CD47 antibody disclosed herein. In one embodiment, a polynucleotide sequence encodes a VH and a VL of an anti-CD47 antibody disclosed herein.

One embodiment of the invention provides a vector comprising a polynucleotide sequence encoding an anti-CD47 antibody, or an antigen-binding fragment thereof, disclosed herein. In one embodiment, the vector is an expression vector. In one embodiment, the vector is a cloning vector. One embodiment of the invention provides a host cell comprising the vector.

Methods of Use

The AlivaMab antibodies against CD47, and in particular fully human antibodies incorporating all or portions of the heavy chain and light chain variable regions from the AlivaMab antibodies, may have utility for the treatment of human disease including, but not limited to, diseases in oncology and ischemia-reperfusion injury (IRI). As the understanding of CD47 biology and disease association becomes better known, it is expected that opportunities for human clinical therapeutic indications may expand. In particular, oncological diseases and disorders and IRI prevention are contemplated.

An anti-CD47 antibody, or antigen-binding fragment thereof, disclosed herein may be used in research, diagnostic, and/or therapeutic methods. In one embodiment, an anti-CD47 antibody, or antigen-binding fragment thereof, disclosed herein is used to treat diseases and disorders associated with CD47 and/or SIRPα. In one embodiment, an anti-CD47 antibody, or antigen-binding fragment thereof, disclosed herein is used to treat diseases and disorders associated with CD47 overexpression. In one embodiment, an anti-CD47 antibody, or antigen-binding fragment thereof, disclosed herein is used to induce phagocytosis by macrophages. In one embodiment, an anti-CD47 antibody, or antigen-binding fragment thereof, disclosed herein exhibits little to zero hemagglutination of erythrocytes.

Modified Anti-CD47 Antibodies and Compositions

Anti-CD47 antibodies of the present invention, and antigen-binding fragments and variants thereof, may also be conjugated or operably linked to another compound (e.g., therapeutic agent, label, or tag), referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents are contemplated. In one embodiment, the antibody is conjugated or operably linked to a toxin, including but not limited to small molecule toxins and enzymatically active toxins of bacterial, fungal, plant, animal or synthetic origin, including fragments and/or variants thereof.

There are many linking groups known in the art for making antibody conjugates, including, for example, those disclosed in U.S. Pat. No. 5,208,020 or EP Patent 0425235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred.

The present invention further relates to pharmaceutical compositions and methods of use. The pharmaceutical compositions of the present invention include an antibody, or fragment thereof, in a pharmaceutically acceptable carrier. Pharmaceutical compositions may be administered in vivo for the treatment or prevention of a disease or disorder. Furthermore, pharmaceutical compositions comprising an antibody, or a fragment thereof, of the present invention may include one or more agents for use in combination, or may be administered in conjunction with one or more agents. Agents for use in combination with an anti-CD47 antibody disclosed herein include, but are not limited to cytotoxic agents, chemotherapeutic agents, cytokines, anti-angiogenic agents, tyrosine kinase inhibitors, toxins, and radioisotopes.

The present invention also provides kits relating to any of the antibodies, or fragments thereof, and/or methods described herein. Kits of the present invention may include diagnostic or therapeutic agents. A kit of the present invention may further provide instructions for use of a composition or antibody and packaging. A kit of the present invention may include devices, reagents, containers or other components. Furthermore, a kit of the present invention may also require the use of an apparatus, instrument or device, including a computer.

EXAMPLES

Example 1

Generation of Monoclonal Antibodies to CD47

Monoclonal antibodies were prepared in accordance with a general method as described in "Antibodies: A Laboratory Manual" (Harlow and Lane 1988 CSH Press). Two AlivaMab Kappa Mice were immunized using a RIMMS protocol. 50 µg of human CD47 extracellular domain with a histidine- (HIS-) tag (Sino Biological, China) was mixed with 40 µl (first immunization), 20 µl (immunizations 2-4) or 0 µl (final immunization) Gerbu MM adjuvant (C-C Biotech, Valley Center, Calif. #3001-6030) and PBS was added to a final volume of 100 µl. The 50 µg mixture was injected in 20 µl portions in 5 locations per mouse; right and left flanks and right and left shoulder/armpit subcutaneously, and the remaining 20 µl intraperitoneally. This was done 5 times per mouse on days, 1, 4, 7, 9, and 11. On Day 14 mice were sacrificed and terminal materials were collected. Spleens and lymph nodes were prepared and fused with CRL-2016 myeloma cells (ATCC) using a PEG based method as generally described in "Antibodies: A Laboratory Manual" (Harlow and Lane 1988 CSH Press) to establish hybridomas.

Hybridomas were grown in 384-well tissue culture plates and supernatants from individual wells were screened by ELISA for production of antibodies recognizing huCD47. Positive wells were then transferred to 48-well plates, expanded, and supernatants were collected for huCD47 binding confirmation by ELISA. Positive supernatants were also counter-screened against a non-related histidine-tagged protein. One hundred forty-seven (147) ELISA-positive (100× above background) were identified. Sixty-seven (67) hybridoma lines confirmed to bind CD47 specifically by ELISA were picked at random and single-cell cloned into 96-well plates. All 67 hybridoma lines were stable and single-cell cloned and were re-confirmed to produce monoclonal antibody binding to huCD47 in ELISA. Sixty-one hybridoma lines were advanced for subsequent analysis. The isotypes of the mouse Fc on the AlivaMab antibodies were determined using standard commercially available isotyping kits.

Example 2

Screen for Neutralization of Binding of SIRP α to CD47 in ELISA

Sixty-one hybridoma clones were screened for inhibition of SIRP α binding to CD47. Briefly, recombinant CD47-Fc (Sino Biologics) at 1 µg/ml in phosphate-buffered saline (PBS) plus 0.05% TWEEN was coated onto the bottom of 96-well ELISA plates overnight. The plates were washed two-times in PBS and non-specific binding was blocked by one-hour incubation at room temperature with SuperBlock™. Unrelated antibody isotype controls (negative control) and recombinant blocking CD47 monoclonal antibody B6H12 (positive control) were used at 20 µg/ml. Supernatants from cloned hybridoma lines were added at a 1:2 dilution. All samples were in triplicate. The antibodies were incubated with plate-bound human CD47-Fc for 15 minutes at room temperature and then recombinant human HIS-tagged SIRP α was added at 2 µg/ml. The plates were incubated for 1 hour at room temperature and then washed two times with PBS plus 0.05% TWEEN. An anti-HIS-tag antibody was added and incubated for one hour. The anti-HIS-tag antibody detects HIS-tagged SIRP α bound to human CD47-Fc. The plates were incubated for 1 hour at room temperature and then washed two times with PBS plus 0.05% TWEEN. SuperSignal™ at 20 µg/ml was added and binding signal detected on a plate reader. The lower the RU signal the greater the ability of antibody to block binding of human CD47 to SIRP α. Sixteen of the 61 antibodies tested substantially or completely blocked binding of human CD47 to SIRP α (FIG. 1).

TABLE 3

CD47 AlivaMabs That Block the Binding
of Human CD47 to Human SIRP α
LIST OF MONOCLONAL ANTIBODIES THAT BLOCK
HUMAN CD47 BINDING TO SIRP α

5
10
14
85
87
91
101
102
106
107
139
144
151
153
161
164

Example 3

Screen for Binding to Native Human CD47 Expressed in Cell Surface

Figure 2:
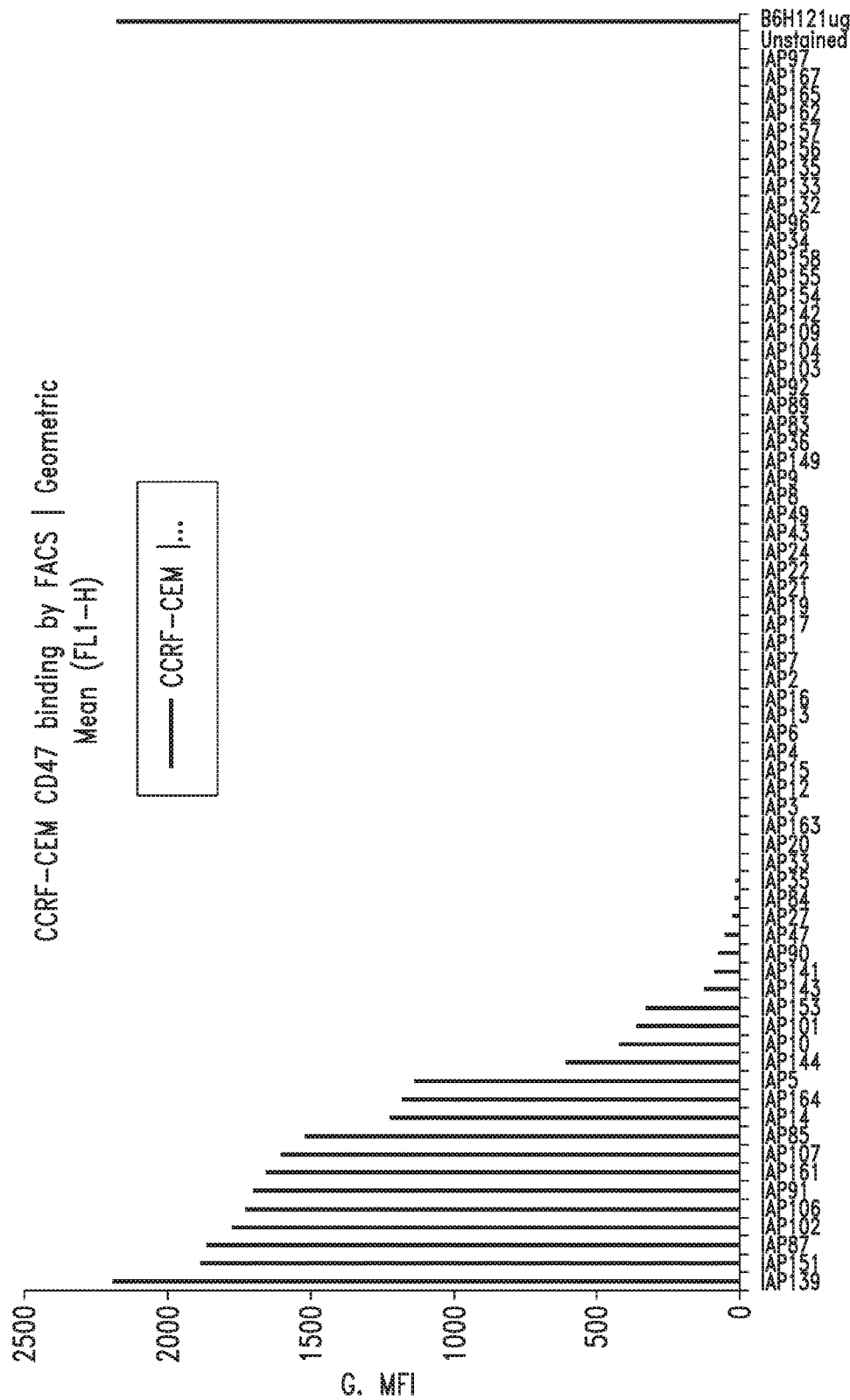
FIG. 2 shows anti-CD47 antibody binding to native human CD47 expressed on the surface of CCRF-CEM human tumor cell line, a T lymphoblastoid cell line (ATCC CCL-119) as detected by flow cytometry.

The sixty-one monoclonal antibodies were screened for binding to native human CD47 expressed on the surface of the CCRF-CEM human tumor cell line, a T lymphoblastoid cell line (ATCC CCL-119) by flow cytometry (FACS). Twenty of 65 antibodies tested bound to native CD47 as assessed by FACS. Sixteen were assessed as strong binders and four were assessed as weak binders (FIG. 2). Binding in the FACS correlated with inhibition of binding to SIRP α. The low level of FACS positive binders to human CD47 expressed on the surface of human cells suggests that the recombinant human CD47 used for immunization and screening of the hybridomas poorly represented the native conformation of human CD47.

TABLE 4

CD47 AlivaMabs That Bind to Native CD47 on
a Human Cell Line Correlate with Neutralization
of Binding of Human CD47 to Human SIRP α

| mAb Clone ID | LIST OF MONOCLONAL ANTIBODIES THAT BLOCK HUMAN CD47 BINDING TO SIRP α | BINDING TO CD47 IN FACS ASSAY |
|---|---|---|
| 5 | + | + |
| 10 | + | + |
| 14 | + | + |
| 85 | + | + |
| 87 | + | + |
| 91 | + | + |
| 101 | + | + |
| 102 | + | + |
| 106 | + | + |
| 107 | + | + |
| 139 | + | + |
| 144 | + | + |
| 151 | + | + |
| 153 | + | + |
| 161 | + | + |
| 164 | + | + |
| 143 | +/− | +/− |
| 141 | − | +/− |
| 90 | +/− | +/− |
| 47 | − | +/− |

Example 4

Determination of IC50 Values Neutralization of Binding of SIRP α to CD47 in ELISA Concentrated monoclonal antibody for the top 18 anti-CD47 mAbs was used in the CD47-SIRP α neutralization assay to determine IC50 values. An assay format similar to that in Example 2 was performed, using an 8 fold 1:2 dilution series of antibody, from 10 µg/ml to 0.005 µg/ml. IC50 values were calculated using PRISM software. The sixteen antibodies with the lowest IC50 also completely block binding of CD47 binding to SIRP α.

TABLE 5

Antibody Isotype and IC50 Values for Neutralization
of Binding of Human CD47 to Human SIRP α

| mAb ID | Isotype | IC50 (nM) |
|---|---|---|
| 151 | IgG1 | 2.0 |
| 91 | IgG1 | 2.1 |
| 139 | IgG1 | 2.2 |
| 102 | IgG1 | 2.3 |
| 107 | IgG1 | 2.7 |
| 106 | IgG1 | 2.9 |
| 87 | IgG1 | 3.0 |
| 161 | IgG1 | 3.0 |
| 5 | IgG1 | 3.5 |
| 14 | IgG1 | 3.5 |
| 10 | IgG2a | 4.7 |
| 164 | IgG1 | 4.8 |
| 85 | IgG1 | 4.9 |
| 144 | IgG1 | 10 |
| 101 | IgG1 | 15 |
| 153 | IgG1 | 27.9 |
| 90 | IgG1 | 53.6 |
| 143 | IgG1 | 96 |

Example 5

Induction of Macrophage Phagocytosis of Cells from a Human Tumor Cell Line

Figure 3:
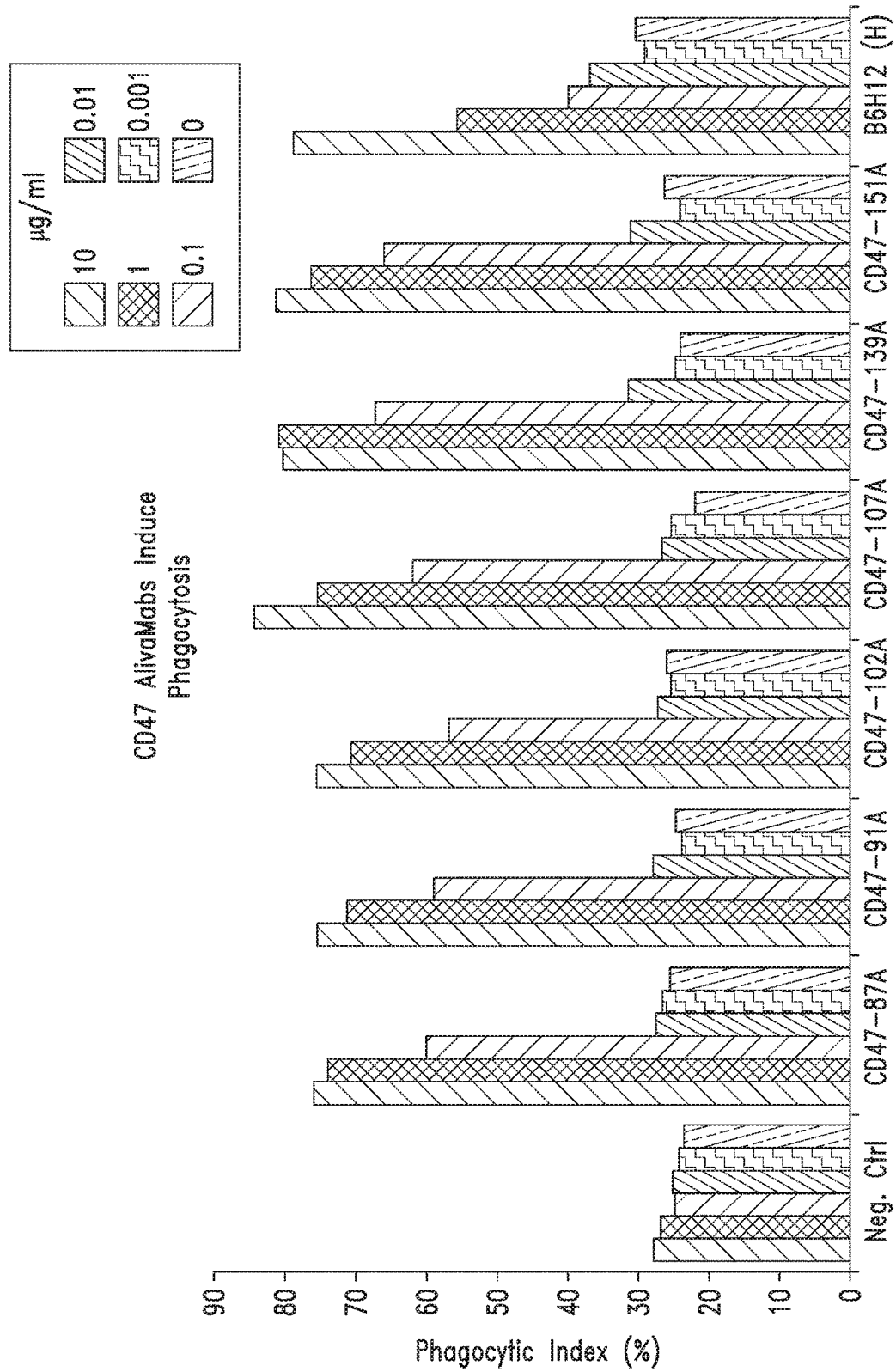
FIG. 3 shows anti-CD47 mAbs potently induced phagocytosis of CCRF-CEM human tumor cells by macrophages.

Neutralization of the binding of CD47 expressed on target cells to SIRP α expressed macrophages can induce macrophages to phagocytose the target cell. A cell based fluorescent assay similar to that used in WO 2013/119714 was used to assess a panel of the top five anti-CD47 mAbs that neutralize with the highest IC50 CD47/SIRP α binding for the ability to induce phagocytosis of a target human tumor cell line. CD47-expressing CCRF-CEM cells were incubated with 0.3 uM CFSE for 15 minutes at 37° C. and washed with PBS to remove CFSE. CFSE-labeled CCRF-CEM cells fluoresce in the FL-1 channel in FACS. CFSE-labeled CCRF-CEM cells were incubated with monocyte-derived human macrophages for 3 hr at 37° C. at a ratio of 4:1 CCRF-CEM cell to macrophage, with or without anti-CD47 mAbs. Monocyte-derived human macrophages are adherent. Non-adherent cells on the plate were washed away with PBS and the adherent cells were scraped off of the bottom of the plate. Macrophages with stained with anti-CD14 antibody conjugated with dye to fluoresce in the FL-4 channel in FACS. Macrophages that had phagocytosed the CCRF-CEM cells would also have ingested the CFSE dye and would fluoresce in the FL-1 channel in FACS. Double-positive FL-4+/FL-1+ cells are macrophages that have phagocytosed CFSE-labeled CCRF-CEM cells. The CD47 mAbs, antibody B6H12 (as a positive control) and an irrelevant mouse IgG1 mAb (as a negative control) were tested for the ability to induce phagocytosis at five concentration, of 1:10 dilutions from 10 µg/ml to 0.001 µg/ml. The data were expressed as the phagocytotic index, the percentage of CD14+ (FL-4+) cells that were also positive in the FL-1 channel in FACS (had ingested CFSE through phagocytosis of CFSE-labeled CCRF-CEM cells). Other mAbs in the panel that neutralize CD47/SIRP α binding in ELISA may also exhibit potent induction of macrophage phagocytosis of human tumor cells. The data show that mAbs potently induce phagocytosis of the CCRF-CEM human tumor cells by macrophages and that they do so more potently than control mAb B6H12. At a concentration of 0.1 µg/ml, the mAbs are still exhibiting significant induction of phagocytosis while the activity of B6H12 is approaching baseline established by the negative control mAb (FIG. 3).

Example 6

Screen for Induction of Hemagglutination of Human Erythrocytes by Monoclonal Antibodies Against Human CD47

Figure 4:
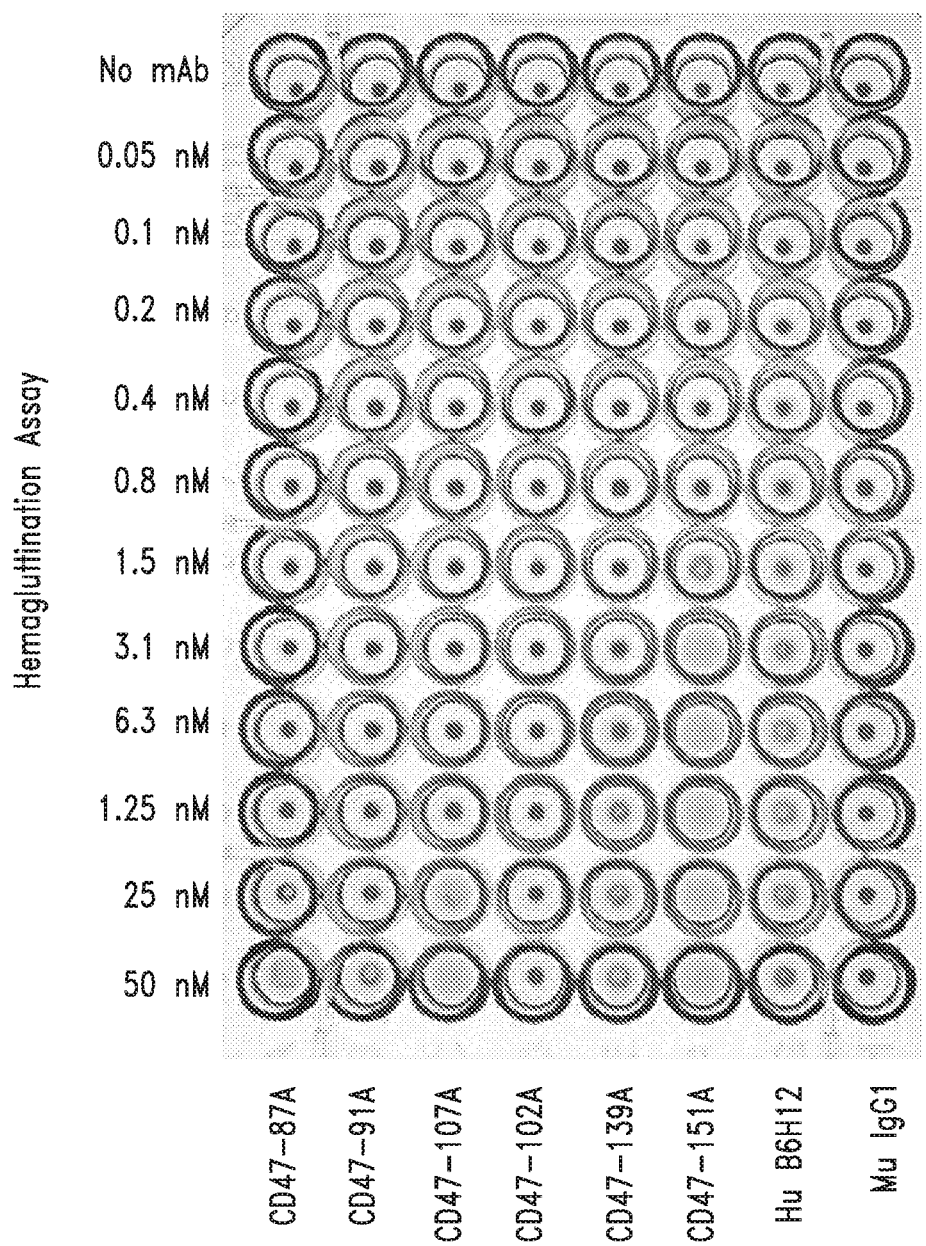
FIG. 4 shows anti-CD47 mAbs with little to zero induced hemagglutination of human erythrocytes (RBCs).

The antibodies were screened for their induction of hemagglutination of human erythrocytes (RBCs). Human RBCs were diluted 1:10 in PBS and incubated at 37° C. with a 1:2 dilution of antibody from 50 nM to 0.05 nM. Humanized antibody B6H12 was used as a positive control and mouse IgG1 was used as a negative control. RBCs that have not undergone hemagglutination appear as a tight red dot. Hemagglutinated RBCs are more diffuse. Data are shown in FIG. 4. Antibody 102 exhibited no evident hemagglutination at the maximal tested concentration of 50 nM. In assays using higher concentrations, antibodies of the invention, including Antibody 102, will show no evident hemagglutination at concentrations up to 500 nM. Antibody 91 exhibited no evident hemagglutination at concentration of 25 nM and a small amount of hemagglutination at 50 nM. Therefore, antibody 102 is a therapeutic candidate antibody as it exhibits potent induction of phagocytosis of CCRF-CEM cells while exhibiting no hemagglutination of RBCs. Antibody 91 is also a candidate. Antibodies 91, 102, 87, 107 and 139 all appeared to be superior to humanized B6H12 as they exhibited more potent induction of phagocytosis of CCRF-CEM cells, while exhibiting no or lower hemagglutination of RBCs at higher concentrations than humanized B6H12. No prozone effect of hemagglutination was observed with any of the AlivaMab CD47 mAbs. Other AlivaMab antibodies exhibiting neutralization of CD47/SIRP α binding and induction of phagocytosis of human tumor cells by macrophages also showed no or limited hemagglutination at high concentrations and are therapeutic candidates.

Example 7

Sequences of Anti-CD47 VH and VL

Total RNA was extracted from hybridomas producing anti-CD47 monoclonal antibodies using the Qiagen RNeasy Mini kit (Cat No. 74104), followed by 5' RACE, using the 5' RACE system kit (Life Technologies, US cat #18734-058) with the following 3' gene specific primers IgG 5'-GGTTCGGGGAAGTAGTCCTTGACC-3' (SEQ ID NO:337) and IgK 5'-CCGATTGGAGGGCGTTATCCAC-3' (SEQ ID NO:338). RACE products were gel purified and cloned into pCR4-TOPO using TOPO TA cloning kit for sequencing with One Shot Top 10 chemically competent *E. coli* (Life Technologies, US Cat #K4575-01). Sequencing of vector containing colonies was performed by Sequetech (Mountain View, Calif.) using M13F or M13R sequencing primers. The reported nucleotide sequences start at the first nucleotide in the first codon for the amino terminal amino acid in framework 1. The reported polypeptide sequences are based on an in silico translation of the nucleic acid sequence and start at the first amino acid at the amino terminus of framework 1.

Example 8

Epitope Binning

A competition ELISA was performed to establish competitive binding bins. ELISA plates were coated with 1 µg/ml huCD47 protein (Sino Biological, China 10161-H08H) and blocked with Superblock (Thermo Scientific #37518). After washing, wells were incubated with an AlivaMab monoclonal antibody representing one of seven unique competition bins. After 1 hour the wells were washed and incubated with individual clonal anti-huCD47 AlivaMab hybridoma supernatants. After another hour the wells were washed and incubated with a specific secondary antibody that either recognized human kappa light chain (LC) or human lambda LC depending on which AlivaMab Mouse supernatants were being detected (Southern Biotech Goat X hu kappa LC #2061-05 or Bethyl Goat X hu lambda LC #A80-116P) and detected with Supersignal ELISA Pico Chemiluminescent substrate (Thermo Scientific—Product #37069) (Tables 5 and 6). Individual AlivaMab Mouse antibodies that were able to bind in the presence of a mouse antibody are considered to be in a unique epitope bin from that particular mouse antibody. Individual AlivaMab Mouse antibodies that were unable to bind in the presence of a mouse antibody are considered to be in the same epitope bin as that particular mouse antibody. In this way multiple epitope bins were defined for huCD47 binding antibodies (Tables 3 and 6, FIG. 5).

TABLE 6

Multiple Epitope Bins

| | Bin 1 | Bin 2 | Bin 3 | Bin 4 | Bin 5 | Bin 6 | Bin 7 |
|---|---|---|---|---|---|---|---|
| All CD47 AlivaMabs by bin | 12 | 7 | 5 | 7 | 1 | 26 | 3 |
| Functional mAbs Assigned to Epitope Bin | 5 | 107 | | | | 91 | 151 |
| | 14 | 161 | | | | 106 | 139 |
| | 10 | 85 | | | | 87 | 102 |
| | 144 | 101 | | | | 164 | |
| | 153 | | | | | | |
| | 90 | | | | | | |
| | 143 | | | | | | |

Example 9

Affinity Determination

Affinity was determined for five selected AlivaMab Mouse monoclonal hybridoma supernatants (Biosensor Tools, Salt Lake City, Utah). Binding kinetics were measured at 25° C. using a BioRad ProteOn XPR36 optical biosensor equipped with GLM sensor chips and equilibrated with running buffer (HBS, 0.005% TWEEN-20, 0.1 mg/mL BSA, pH 7.4).

The tested antibodies were AlivaMab antibodies: 91, 102, 107, 139 and 151. Kinetics of binding each mAb to recombinant human CD47 (Novoprotein cat no. C321, lot no. 0329689) was measured.

The analyses were performed by capture of the mouse antibodies on sensor surfaces coated with an anti-mouse capturing agent.

CD47 Binding to Five AlivaMab Anti-CD47 Antibodies

The five antibodies were captured to densities of 850-1030 RU onto an anti-mouse Fc surface. CD47 was tested in a three-fold dilution series starting at 100 nM.

These binding data were also fit to a 1:1 interaction model:

Within the panel of AlivaMab Mouse anti-CD47 antibodies, there are antibodies with KD values below a nanomolar and KD values in the low nanomolar range, and with fast $k_{on}$ and slow $k_{off}$ rates (Tables 7-9).

TABLE 7

Binding Kinetics of Anti-CD47 IgG AlivaMab mAbs

| mAb | ka ($M^{-1}s^{-1}$) | kd ($s^{-1}$) | $K_D$ (pM) |
|---|---|---|---|
| 91 | 7.2(2)e6 | 1.111(3)e−3 | 154.4(7) pM |
| 102 | 6.9(2)e6 | 2.21(7)e−3 | 320(3) pM |
| 107 | 5.7(1)e6 | 9.3(2)e−4 | 163(1) pM |
| 139 | 1.18(6)e6 | 1.00e−5* | 8.5(4) pM |
| 151 | 8.7(4)e6 | 08.9(4)e−3 | 1.002(8) nM |

*No decay was detected in the responses from the 139A surface during the dissociation phase. This indicates the complex dissociated very little during this time. Therefore, the dissociation rate constant was fixed at $1 \times 10^{-5}$ $s^{-1}$ during the fitting process so the KD must be considered a rough estimate.

Table 8 summarizes the parameters determined from these measurements.

TABLE 8

Summary of Binding Kinetics of Anti-CD47 mAbs
Binding constants determined at 25° C.

| | $k_a$ ($M^{-1}s^{-1}$) | $k_d$ ($s^{-1}$) | $K_D$ (pM) |
|---|---|---|---|
| m91A | 7.2(2)e6 | 1.11(3)e−3 | 150(10) |
| m102A | 6.9(2)e6 | 2.21(7)e−3 | 320(10) |
| m107A | 5.7(1)e6 | 9.3(2)e−4 | 160(10) |
| m139A | 1.18(6)e6 | 1e−5** | ~9 |
| m151A | 8.7(4)e6 | 8.9(4)e−3 | 1000(100) |

* average of measurements from three antibody surfaces
**this dissociation rate constant was fixed at 1e−5 $s^{-1}$ Another way to compare these five antibodies is to bin and rank them by their dissociation rate constants.

TABLE 9

Binning and Ranking of Anti-CD47 mAbs by Their Dissociation Constants
Antibodies binned by $k_d$'s determined at 25° C.

| fastest ~$10^{-2}$ $s^{-1}$ | ~$10^{-3}$ $s^{-1}$ | ~$4 \times 10^{-4}$ $s^{-1}$ | slowest ≤$10^{-5}$ $s^{-1}$ |
|---|---|---|---|
| m151A | m107A<br>m91A<br>m102A | hB6412<br>hAb6.12 | m139A |

AlivaMab antibody 139A appeared to have a very slow dissociation rate constant.

In summary, CD47 showed binding to all five antibodies, with affinities that ranged from ~10 pM to ~1.5 nM.

The 139A/CD47 complex was so stable that a dissociation rate constant could not be reliably determined from these analyses.

Example 10

AlivaMab Mouse Anti-CD47 mAbs and Their Fully Human Derivatives Bind to and Neutralize CD47 from Cynomolgus Monkey CD47 is cloned and expressed from cynomolgus monkey using standard molecular biological techniques. The recombinant CD47 may be tagged (histidine, Fc) to support efficient purification. The recombinant cynomolgus CD47 may also be transiently or stably expressed on cell lines. The AlivaMab Mouse anti-CD47 mAbs and their human variants are shown to bind to cynomolgus monkey CD47. The AlivaMab Mouse anti-CD47 mAbs and their human variants are shown to neutralize cynomolgus monkey CD47 in assays as described above for human CD47.

Example 11

AlivaMab Mouse Anti-CD47 mAbs and Their Fully Human Derivatives Bind to and Neutralize CD47 from Mouse CD47 is cloned and expressed from mouse using standard molecular biological techniques. The recombinant CD47 may be tagged (histidine, Fc) to support efficient purification. The recombinant mouse CD47 may also be transiently or stably expressed on cell lines. The AlivaMab Mouse anti-CD47 mAbs and their human variants are shown to bind to mouse CD47. The AlivaMab Mouse anti-CD47 mAbs and their human variants are shown to neutralize mouse CD47 in assays as described above for human CD47.

Example 12

Conversion of AlivaMab Mouse Anti-CD47 mAbs to Fully Human

The AlivaMab Mouse anti-CD47 mAbs are easily converted, expressed recombinantly and purified as fully-human antibodies of any isotype. The recombinant fully-human antibody retains all of the characteristics of the parental AlivaMab Mouse antibody. For example, the nucleotide sequences of the heavy and light chain variable region are synthesized into DNA by contract research organization such as Lake Pharma (Belmont Calif.) and then, using vectors for recombinant expression in mammalian cells, the VH cloned in-frame with coding sequences for the human isotype of choice IgG1, IgG2, or IgG4 constant regions and including modified versions thereof that are known in the art and the Vκ cloned in-frame with coding sequences for the human Cκ region. The Fc regions may be modified for either increased or decreased effector function such as C1q binding or FcR binding. In particular the antibody isotype may be human IgG4, which may exhibit lowered antibody dependent cellular cytotoxicity than human IgG1 or human IgG2. The middle hinge and or the Fc of the human IgG4 may be modified (for example, see U.S. Pat. No. 8,911,726 and disclosures and references therein.) IgG4 may also be modified to drive inter-chain disulfide bonds rather intra-chain to better ensure homodimeric IgG4 rather than monomeric or heterodimeric formation (replacement of the middle hinge region with that from human IgG1; mutation S228P/L235E;

mutation of serine 229 to proline (Bloom et al., Protein Sci. (1997) 6:407-15); see also Peters et al., J. Biol. Chem. 2012). Vectors are then transformed into HEK293 cells for expression of recombinant fully human antibody. Fully human IgGκ mAb versions of the selected AlivaMab mAb are purified from tissue culture supernatants using protein A. The fully human versions retain all of the characteristics of the parental chimeric AlivaMab.

In additional examples, the CD47 antibodies will exhibit anti-tumor activities in human tumor xenograft models in mice such as the Raji model of lyphoma. The antibodies will exhibit anti-tumor activities in preventative models and eradication models.

The epitopes of the AlivaMab CD47 antibodies can be epitope mapped by various methods known in the art. The panel of epitopes on CD47 will include linear and conformational epitopes. Key contact amino acids in the epitope can be discerned by site-direct mutagenesis or by solving the crystal structure of the antibody-CD47 binding interaction. The antibodies that neutralize CD47/SIRP α binding will have different epitopes. Some epitopes will overlap structurally and will have some overlapping and some different key contact residues. Some epitopes will be not overlap structurally with epitopes of other antibodies. Unique epitopes will correlate with unique activities of antibodies.

What is claimed is:

1. An isolated anti-CD47 antibody, or an antigen-binding fragment thereof, comprising a) a heavy chain variable region comprising a VHCDR1, a VHCDR2, and a VHCDR3 and b) a light chain variable region comprising a VLCDR1, a VLCDR2, and a VLCDR3, wherein:

i) the VHCDR1 comprises the amino acid sequence of SEQ ID NO: 22, the VHCDR2 comprises the amino acid sequence of SEQ ID NO: 43, the VHCDR3 comprises the amino acid sequence of SEQ ID NO: 64, the VLCDR1 comprises the amino acid sequence of SEQ ID NO: 106, the VLCDR2 comprises the amino acid sequence of SEQ ID NO: 127, and the VLCDR3 comprises the amino acid sequence of SEQ ID NO: 148;

ii) the VHCDR1 comprises the amino acid sequence of SEQ ID NO: 23, the VHCDR2 comprises the amino acid sequence of SEQ ID NO: 44, the VHCDR3 comprises the amino acid sequence of SEQ ID NO: 65, the VLCDR1 comprises the amino acid sequence of SEQ ID NO: 107, the VLCDR2 comprises the amino acid sequence of SEQ ID NO: 128, and the VLCDR3 comprises the amino acid sequence of SEQ ID NO: 149;

iii) the VHCDR1 comprises the amino acid sequence of SEQ ID NO: 24, the VHCDR2 comprises the amino acid sequence of SEQ ID NO: 45, the VHCDR3 comprises the amino acid sequence of SEQ ID NO: 66, the VLCDR1 comprises the amino acid sequence of SEQ ID NO: 108, the VLCDR2 comprises the amino acid sequence of SEQ ID NO: 129, and the VLCDR3 comprises the amino acid sequence of SEQ ID NO: 150;

iv) the VHCDR1 comprises the amino acid sequence of SEQ ID NO: 25, the VHCDR2 comprises the amino acid sequence of SEQ ID NO: 46, the VHCDR3 comprises the amino acid sequence of SEQ ID NO: 67, the VLCDR1 comprises the amino acid sequence of SEQ ID NO: 109, the VLCDR2 comprises the amino acid sequence of SEQ ID NO: 130, and the VLCDR3 comprises the amino acid sequence of SEQ ID NO: 151;

v) the VHCDR1 comprises the amino acid sequence of SEQ ID NO: 26, the VHCDR2 comprises the amino acid sequence of SEQ ID NO: 47, the VHCDR3 comprises the amino acid sequence of SEQ ID NO: 68, the VLCDR1 comprises the amino acid sequence of SEQ ID NO: 110, the VLCDR2 comprises the amino acid sequence of SEQ ID NO: 131, and the VLCDR3 comprises the amino acid sequence of SEQ ID NO: 152;

vi) the VHCDR1 comprises the amino acid sequence of SEQ ID NO: 27, the VHCDR2 comprises the amino acid sequence of SEQ ID NO: 48, the VHCDR3 comprises the amino acid sequence of SEQ ID NO: 69, the VLCDR1 comprises the amino acid sequence of SEQ ID NO: 111, the VLCDR2 comprises the amino acid sequence of SEQ ID NO: 132, and the VLCDR3 comprises the amino acid sequence of SEQ ID NO: 153;

vii) the VHCDR1 comprises the amino acid sequence of SEQ ID NO: 28, the VHCDR2 comprises the amino acid sequence of SEQ ID NO: 49, the VHCDR3 comprises the amino acid sequence of SEQ ID NO: 70, the VLCDR1 comprises the amino acid sequence of SEQ ID NO: 112, the VLCDR2 comprises the amino acid sequence of SEQ ID NO: 133, and the VLCDR3 comprises the amino acid sequence of SEQ ID NO: 154;

viii) the VHCDR1 comprises the amino acid sequence of SEQ ID NO: 29, the VHCDR2 comprises the amino acid sequence of SEQ ID NO: 50, the VHCDR3 comprises the amino acid sequence of SEQ ID NO: 71, the VLCDR1 comprises the amino acid sequence of SEQ ID NO: 113, the VLCDR2 comprises the amino acid sequence of SEQ ID NO: 134, and the VLCDR3 comprises the amino acid sequence of SEQ ID NO: 155;

ix) the VHCDR1 comprises the amino acid sequence of SEQ ID NO: 30, the VHCDR2 comprises the amino acid sequence of SEQ ID NO: 51, the VHCDR3 comprises the amino acid sequence of SEQ ID NO: 72, the VLCDR1 comprises the amino acid sequence of SEQ ID NO: 114, the VLCDR2 comprises the amino acid sequence of SEQ ID NO: 135, and the VLCDR3 comprises the amino acid sequence of SEQ ID NO: 156;

x) the VHCDR1 comprises the amino acid sequence of SEQ ID NO: 31, the VHCDR2 comprises the amino acid sequence of SEQ ID NO: 52, the VHCDR3 comprises the amino acid sequence of SEQ ID NO: 73, the VLCDR1 comprises the amino acid sequence of SEQ ID NO: 115, the VLCDR2 comprises the amino acid sequence of SEQ ID NO: 136, and the VLCDR3 comprises the amino acid sequence of SEQ ID NO: 157;

xi) the VHCDR1 comprises the amino acid sequence of SEQ ID NO: 32, the VHCDR2 comprises the amino acid sequence of SEQ ID NO: 53, the VHCDR3 comprises the amino acid sequence of SEQ ID NO: 74, the VLCDR1 comprises the amino acid sequence of SEQ ID NO: 116, the VLCDR2 comprises the amino acid sequence of SEQ ID NO: 137, and the VLCDR3 comprises the amino acid sequence of SEQ ID NO: 158;

xii) the VHCDR1 comprises the amino acid sequence of SEQ ID NO: 33, the VHCDR2 comprises the amino acid sequence of SEQ ID NO: 54, the VHCDR3 comprises the amino acid sequence of SEQ ID NO: 75, the VLCDR1 comprises the amino acid sequence of SEQ ID NO: 117, the VLCDR2 comprises the amino acid sequence of SEQ ID NO: 138, and the VLCDR3 comprises the amino acid sequence of SEQ ID NO: 159;

xiii) the VHCDR1 comprises the amino acid sequence of SEQ ID NO: 34, the VHCDR2 comprises the amino acid sequence of SEQ ID NO: 55, the VHCDR3 comprises the amino acid sequence of SEQ ID NO: 76, the VLCDR1 comprises the amino acid sequence of SEQ ID NO: 118, the VLCDR2 comprises the amino acid sequence of SEQ ID NO: 139, and the VLCDR3 comprises the amino acid sequence of SEQ ID NO: 160;

xiv) the VHCDR1 comprises the amino acid sequence of SEQ ID NO: 35, the VHCDR2 comprising the amino acid sequence of SEQ ID NO: 56, the VHCDR3 comprises the amino acid sequence of SEQ ID NO: 77, the VLCDR1 comprises the amino acid sequence of SEQ ID NO: 119, the VLCDR2 comprises the amino acid sequence of SEQ ID NO: 140, and the VLCDR3 comprises the amino acid sequence of SEQ ID NO: 161;

xv) the VHCDR1 comprises the amino acid sequence of SEQ ID NO: 36, the VHCDR2 comprises the amino acid sequence of SEQ ID NO: 57, the VHCDR3 comprises the amino acid sequence of SEQ ID NO: 78, the VLCDR1 comprises the amino acid sequence of SEQ ID NO: 120, the VLCDR2 comprises the amino acid sequence of SEQ ID NO: 141, and the VLCDR3 comprises the amino acid sequence of SEQ ID NO: 162;

xvi) the VHCDR1 comprises the amino acid sequence of SEQ ID NO: 37, the VHCDR2 comprises the amino acid sequence of SEQ ID NO: 58, the VHCDR3 comprises the amino acid sequence of SEQ ID NO: 79, the VLCDR1 comprises the amino acid sequence of SEQ ID NO: 121, the VLCDR2 comprises the amino acid sequence of SEQ ID NO: 142, and the VLCDR3 comprises the amino acid sequence of SEQ ID NO: 163;

xvii) the VHCDR1 comprises the amino acid sequence of SEQ ID NO: 38, the VHCDR2 comprises the amino acid sequence of SEQ ID NO: 59, the VHCDR3 comprises the amino acid sequence of SEQ ID NO: 80, the VLCDR1 comprises the amino acid sequence of SEQ ID NO: 122, the VLCDR2 comprises the amino acid sequence of SEQ ID NO: 143, and the VLCDR3 comprises the amino acid sequence of SEQ ID NO: 164;

xviii) the VHCDR1 comprises the amino acid sequence of SEQ ID NO: 39, the VHCDR2 comprises the amino acid sequence of SEQ ID NO: 60, the VHCDR3 comprises the amino acid sequence of SEQ ID NO: 81, the VLCDR1 comprises the amino acid sequence of SEQ ID NO: 123, the VLCDR2 comprises the amino acid sequence of SEQ ID NO: 144, and the VLCDR3 comprises the amino acid sequence of SEQ ID NO: 165;

xix) the VHCDR1 comprises the amino acid sequence of SEQ ID NO: 40, the VHCDR2 comprises the amino acid sequence of SEQ ID NO: 61, the VHCDR3 comprises the amino acid sequence of SEQ ID NO: 82, the VLCDR1 comprises the amino acid sequence of SEQ ID NO: 124, the VLCDR2 comprises the amino acid sequence of SEQ ID NO: 145, and the VLCDR3 comprises the amino acid sequence of SEQ ID NO: 166;

xx) the VHCDR1 comprises the amino acid sequence of SEQ ID NO: 41, the VHCDR2 comprises the amino acid sequence of SEQ ID NO: 62, the VHCDR3 comprises the amino acid sequence of SEQ ID NO: 83, the VLCDR1 comprises the amino acid sequence of SEQ ID NO: 125, the VLCDR2 comprises the amino acid sequence of SEQ ID NO: 146, and the VLCDR3 comprises the amino acid sequence of SEQ ID NO: 167; or xxi) the VHCDR1 comprises the amino acid sequence of SEQ ID NO: 42, the VHCDR2 comprises the amino acid sequence of SEQ ID NO: 63, the VHCDR3 comprises the amino acid sequence of SEQ ID NO: 84, the VLCDR1 comprises the amino acid sequence of SEQ ID NO: 126, the VLCDR2 comprises the amino acid sequence of SEQ ID NO: 147, and the VLCDR3 comprises the amino acid sequence of SEQ ID NO: 168.

2. The antibody, or antigen-binding fragment thereof, of claim 1, wherein the antibody is human.

3. The antibody, or antigen-binding fragment thereof, of claim 1, wherein the antibody is chimeric.

4. The antibody, or antigen-binding fragment thereof, of claim 1, wherein the antibody is selected from a single-variable domain antibody, single chain antibody, a scFv, a bispecific antibody, a multi-specific antibody, a Fab, a F(ab')2, a chimeric antigen receptor, and a whole antibody.

5. The antibody, or antigen-binding fragment thereof, of claim 1, wherein the VHCDR1 comprises the amino acid sequence of SEQ ID NO:26, the VHCDR2 comprises the amino acid sequence of SEQ ID NO:47, the VHCDR3 comprises the amino acid sequence of SEQ ID NO: 68, the VLCDR1 comprises the amino acid sequence of SEQ ID NO: 110, the VLCDR2 comprises the amino acid sequence of SEQ ID NO: 131, and the VLCDR3 comprises the amino acid sequence of SEQ ID NO: 152.

6. The antibody, or antigen-binding fragment thereof, of claim 1, wherein the VHCDR1 comprises the amino acid sequence of SEQ ID NO:28, the VHCDR2 comprises the amino acid sequence of SEQ ID NO:49, the VHCDR3 comprises the amino acid sequence of SEQ ID NO:70, the VLCDR1 comprises the amino acid sequence of SEQ ID NO: 112, the VLCDR2 comprises the amino acid sequence of SEQ ID NO: 133, and the VLCDR3 comprises the amino acid sequence of SEQ ID NO: 154.

7. The antibody, or antigen-binding fragment thereof, of claim 1, wherein the VHCDR1 comprises the amino acid sequence of SEQ ID NO:30, the VHCDR2 comprises the amino acid sequence of SEQ ID NO:51, the VHCDR3 comprises the amino acid sequence of SEQ ID NO: 72, the VLCDR1 comprises the amino acid sequence of SEQ ID NO: 114, the VLCDR2 comprises the amino acid sequence of SEQ ID NO: 135, and the VLCDR3 comprises the amino acid sequence of SEQ ID NO: 156.

8. The antibody, or antigen-binding fragment thereof, of claim 1, wherein the VHCDR1 comprises the amino acid sequence of SEQ ID NO:32, the VHCDR2 comprises the amino acid sequence of SEQ ID NO:53, the VHCDR3 comprises the amino acid sequence of SEQ ID NO:74, the VLCDR1 comprises the amino acid sequence of SEQ ID NO: 116, the VLCDR2 comprising the amino acid sequence of SEQ ID NO: 137, and the VLCDR3 comprises the amino acid sequence of SEQ ID NO: 158.

9. The antibody, or antigen-binding fragment thereof, of claim 1, wherein the VHCDR1 comprises the amino acid sequence of SEQ ID NO:33, the VHCDR2 comprises the amino acid sequence of SEQ ID NO:54, the VHCDR3 comprises the amino acid sequence of SEQ ID NO:75, the VLCDR1 comprises the amino acid sequence of SEQ ID NO: 117, the VLCDR2 comprises the amino acid sequence of SEQ ID NO: 138, and the VLCDR3 comprises the amino acid sequence of SEQ ID NO: 159.

10. The antibody, or antigen-binding fragment thereof, of claim 1, wherein the heavy chain variable region comprises an amino acid sequence selected from SEQ ID NOs: 1-21.

11. The antibody, or antigen-binding fragment thereof, of claim 1, wherein the light chain variable region comprises an amino acid sequence selected from SEQ ID NOs:85-105.

12. A recombinant polynucleotide encoding the antibody, or antigen-binding fragment thereof, of claim 1.

13. An expression vector comprising the recombinant polynucleotide of claim 12.

14. An isolated host cell comprising the expression vector of claim 13.

15. A composition comprising the antibody, or antigen-binding fragment thereof, of claim 1 and a physiologically acceptable carrier.

* * * * *

SEQUENCE LISTING

```
<160> NUMBER OF SEQ ID NOS: 338

<210> SEQ ID NO 1
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Lys Gly Gly Thr Asp Tyr Trp Gly Gln Gly Thr Leu Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

Lys Leu Ser Ser Val Thr Ala Ala Asp Thr Ala Val Tyr Tyr Cys Ala
            85                  90                  95

Arg Lys Lys Gly Ala Phe Asp Ile Trp Gly Gln Gly Thr Met Val Thr
            100                 105                 110

Val Ser Ser
        115

<210> SEQ ID NO 3
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Lys Arg Gly Leu Asp Ile Trp Gly Gln Gly Thr Met Val Thr Val
            100                 105                 110

Ser Ser

<210> SEQ ID NO 4
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 4

Gln Val Gln Leu Gln Glu Ser Gly Pro Gly Leu Val Lys Ala Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Ala Gly Lys Gly Leu Glu Trp Ile
        35                  40                  45

Gly Arg Ile Tyr Asn Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gln Thr Tyr Leu Asp Tyr Trp Gly Gln Gly Thr Leu Val Thr Val
            100                 105                 110

Ser Ser

<210> SEQ ID NO 5
<211> LENGTH: 115

<212> TYPE: PRT
<213> ORGANISM: Artificial Sequence
<220> FEATURE:
<223> OTHER INFORMATION: Made in Lab - synthesized VH sequence

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Lys Arg Ala Phe Leu Asp Tyr Trp Gly Gln Gly Thr Leu Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr His Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Phe Tyr Cys Ala
                85                  90                  95

Arg Gly Arg Arg Ala Leu Thr Ala Trp Gly Gln Gly Thr Leu Val Thr
            100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 7

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Thr Tyr
            20                  25                  30

Tyr Trp Ser Trp Ile Arg Gln Pro Gly Lys Gly Leu Glu Trp Ile
        35                  40                  45

Gly Tyr Ile Tyr Tyr Ser Gly Thr Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Arg Asp Ala Phe Asp Ile Trp Gly Gln Gly Thr Met Val Thr
                100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 8

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Phe Tyr
            20                  25                  30

Tyr Trp Thr Trp Ile Arg Gln Pro Pro Gly Lys Gly Leu Glu Trp Ile
        35                  40                  45

Gly Phe Ile Tyr Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Arg Gly Ala Leu Thr Ala Trp Gly Gln Gly Thr Leu Val Thr
                100                 105                 110

Val Ser Ser
        115

<210> SEQ ID NO 9
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 9

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Asn Tyr Asn Pro Ser Leu Lys
 50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Lys Arg Asp Thr Phe Asp Ile Trp Gly Gln Gly Thr Met Val Thr
            100                 105                 110

Val Ser Ser
    115

<210> SEQ ID NO 10
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 10

Gln Val Gln Leu Gln Gly Ser Gly Pro Gly Leu Val Lys Pro Ser Glu
  1               5                  10                  15

Thr Leu Ser Leu Thr Cys Thr Val Ser Gly Gly Ser Ile Asn Asn Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Ser Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Lys Arg Asp Ala Phe Asp Ile Trp Gly Gln Gly Thr Met Val Thr
            100                 105                 110

Val Ser Ser
    115

<210> SEQ ID NO 11
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 11

Gln Val Gln Leu Gln Glu Ser Gly Pro Gly Leu Met Lys Pro Ser Glu
  1               5                  10                  15

Thr Leu Ser Leu Thr Cys Thr Val Ser Gly Gly Ser Ile Ser Ser Tyr
                 20                  25                  30

Tyr Trp Thr Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Arg Gly Ala Leu Thr Ala Trp Gly Gln Gly Thr Leu Val Thr
            100                 105                 110
```

```
Val Ser Ser
        115

<210> SEQ ID NO 12
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Arg Tyr Phe Asp Leu Trp Gly Arg Gly Thr Leu Val Thr Val
            100                 105                 110

Ser Ser

<210> SEQ ID NO 13
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Arg
    50                  55                  60

Ser Arg Val Thr Ile Ser Val Asp Thr Ser Lys Asn Gln Phe Ser Leu
65                  70                  75                  80

Lys Leu Ser Ser Val Ala Ala Ala Asp Thr Ala Val Tyr Tyr Cys Ala
                85                  90                  95

Arg Gln Lys Gly Met Asp Val Trp Gly Gln Gly Thr Thr Val Thr Val
            100                 105                 110

Ser Ser

<210> SEQ ID NO 14
<211> LENGTH: 115
<212> TYPE: PRT
<213> ORGANISM: Artificial Sequence
<220> FEATURE:
<223> OTHER INFORMATION: Made in Lab - synthesized VH sequence
```

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Arg Gly Glu Phe Asp Tyr Trp Gly Gln Gly Thr Leu Val Thr
            100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Arg Lys Tyr Phe Asp Tyr Trp Gly Gln Gly Thr Leu Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Tyr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Arg Ser Ser Tyr Asp Tyr Trp Gly Gln Gly Thr Leu Val Thr
                100                 105                 110

Val Ser Ser
        115

<210> SEQ ID NO 17
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Arg Tyr Phe Asp Leu Trp Gly Arg Gly Thr Leu Val Thr Val
                100                 105                 110

Ser Ser

<210> SEQ ID NO 18
<211> LENGTH: 115
<212> TYPE: PRT
<213> ORGANISM: Artificial Sequence
<220> FEATURE:
<223> OTHER INFORMATION: Made in Lab - synthesized VH sequence

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Val Tyr Tyr Ser Gly Gly Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Lys Arg Gly Thr Phe Asp Tyr Trp Gly Gln Gly Thr Leu Val Thr
                100                 105                 110

Val Ser Ser
         115

<210> SEQ ID NO 19
<211> LENGTH: 114
<212> TYPE: PRT
<213> ORGANISM: Artificial Sequence
<220> FEATURE:
<223> OTHER INFORMATION: Made in Lab - synthesized VH sequence

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Arg Val Phe Asp Leu Trp Gly Arg Gly Thr Leu Val Thr Val
            100                 105                 110

Ser Ser

<210> SEQ ID NO 20
<211> LENGTH: 120
<212> TYPE: PRT
<213> ORGANISM: Artificial Sequence
<220> FEATURE:
<223> OTHER INFORMATION: Made in Lab - synthesized VH sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Arg Asn Trp Asp Ala Phe Asp Ile Trp Gly Gln
            100                 105                 110

Gly Thr Met Val Thr Val Ser Ser
        115                 120

<210> SEQ ID NO 21
<211> LENGTH: 114
<212> TYPE: PRT
<213> ORGANISM: Artificial Sequence
<220> FEATURE:
<223> OTHER INFORMATION: Made in Lab - synthesized VH sequence -continued

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Arg Tyr Phe Asp Tyr Trp Asp Gln Gly Thr Leu Val Thr Val
            100                 105                 110

Ser Ser

<210> SEQ ID NO 22
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 22

Gly Gly Ser Ile Ser Ser Tyr Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 23

Gly Gly Ser Ile Arg Thr Tyr Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 24

Gly Gly Ser Ile Ser Ser Tyr Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 25

Gly Gly Ser Ile Ser Gly Tyr Tyr
1               5

<210> SEQ ID NO 26

<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 26

Gly Gly Ser Ile Ser Ser Tyr Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 27

Gly Gly Ser Ile Asn Asn Tyr Tyr
1               5

<210> SEQ ID NO 28
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 28

Gly Gly Ser Ile Ser Thr Tyr Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 29

Gly Gly Ser Ile Ser Phe Tyr Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 30

Gly Gly Ser Ile Ser Asn Tyr Tyr
1               5

<210> SEQ ID NO 31
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 31

Gly Gly Ser Ile Asn Asn Tyr Tyr
1               5

<210> SEQ ID NO 32
<211> LENGTH: 8

```
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 32

Gly Gly Ser Ile Ser Ser Tyr Tyr
1               5

<210> SEQ ID NO 33
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 33

Gly Gly Ser Ile Ser Asn Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 34

Gly Gly Ser Ile Asn Asn Tyr Tyr
1               5

<210> SEQ ID NO 35
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 35

Gly Gly Ser Ile Ser Ser Tyr Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 36

Gly Gly Ser Ile Ser Ser Tyr Tyr
1               5

<210> SEQ ID NO 37
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 37

Gly Gly Ser Ile Asn Tyr Tyr Tyr
1               5

<210> SEQ ID NO 38
<211> LENGTH: 8
<212> TYPE: PRT
```

```
<213> ORGANISM: Artificial Sequence
<220> FEATURE:
<223> OTHER INFORMATION: Made in Lab - Synthesized VHCDR1 sequence

<400> SEQUENCE: 38

Gly Gly Ser Ile Ser Ser Tyr Tyr
1               5

<210> SEQ ID NO 39
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 39

Gly Gly Ser Ile Ser Ser Tyr Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 40

Gly Gly Ser Ile Ser Ser Tyr Tyr
1               5

<210> SEQ ID NO 41
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 41

Gly Tyr Thr Phe Thr Gly Tyr Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: Made in Lab - Synthesized VHCDR1 sequence

<400> SEQUENCE: 42

Gly Gly Ser Ile Ser Ser Tyr Tyr
1               5

<210> SEQ ID NO 43
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 43

Ile Tyr Tyr Ser Gly Ser Thr
1               5

<210> SEQ ID NO 44
<211> LENGTH: 7
<212> TYPE: PRT
<213> ORGANISM: Artificial Sequence
```

```
<220> FEATURE:
<223> OTHER INFORMATION: Made in Lab - Synthesized VHCDR2 sequence

<400> SEQUENCE: 44

Ile Tyr Tyr Ser Gly Ser Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 45

Ile Tyr Tyr Ser Gly Ser Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 46

Ile Tyr Asn Ser Gly Ser Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 47

Ile Tyr Tyr Ser Gly Ser Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 48

Ile Tyr Tyr Ser Gly Ser Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 49

Ile Tyr Tyr Ser Gly Thr Thr
1               5

<210> SEQ ID NO 50
<211> LENGTH: 7
<212> TYPE: PRT
<213> ORGANISM: Artificial Sequence
<220> FEATURE:
```

<223> OTHER INFORMATION: Made in Lab - Synthesized VHCDR2 sequence

<400> SEQUENCE: 50

Ile Tyr Tyr Ser Gly Ser Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 51

Ile Tyr Tyr Ser Gly Ser Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 52

Ile Tyr Tyr Ser Gly Ser Thr
1               5

<210> SEQ ID NO 53
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 53

Ile Tyr Tyr Ser Gly Ser Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 54

Ile Tyr Tyr Ser Gly Ser Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 55

Ile Tyr Tyr Ser Gly Ser Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 56

Ile Tyr Tyr Ser Gly Thr Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 57

Ile Tyr Tyr Ser Gly Ser Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 58

Ile Tyr Tyr Ser Gly Ser Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 59

Ile Tyr Tyr Ser Gly Ser Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 60

Val Tyr Tyr Ser Gly Gly Thr
1               5

<210> SEQ ID NO 61
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 61

Val Tyr Tyr Ser Gly Ser Thr
1               5

<210> SEQ ID NO 62
<211> LENGTH: 8
<212> TYPE: PRT
<213> ORGANISM: Artificial Sequence
<220> FEATURE:
<223> OTHER INFORMATION: Made in Lab - Synthesized VHCDR2 sequence

```
<400> SEQUENCE: 62

Ile Asn Pro Asn Ser Gly Gly Thr
1               5

<210> SEQ ID NO 63
<211> LENGTH: 7
<212> TYPE: PRT
<213> ORGANISM: Artificial Sequence
<220> FEATURE:
<223> OTHER INFORMATION: Made in Lab - Synthesized VHCDR2 sequence

<400> SEQUENCE: 63

Ile Tyr Tyr Ser Gly Ser Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 64

Ala Arg Gly Lys Gly Gly Thr Asp Tyr
1               5

<210> SEQ ID NO 65
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 65

Ala Arg Lys Lys Gly Ala Phe Asp Ile
1               5

<210> SEQ ID NO 66
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 66

Ala Arg Lys Arg Gly Leu Asp Ile
1               5

<210> SEQ ID NO 67
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 67

Ala Arg Gln Thr Tyr Leu Asp Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence
```

```
<400> SEQUENCE: 68

Ala Arg Lys Arg Ala Phe Leu Asp Tyr
1               5

<210> SEQ ID NO 69
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 69

Ala Arg Gly Arg Arg Ala Leu Thr Ala
1               5

<210> SEQ ID NO 70
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 70

Ala Arg Lys Arg Asp Ala Phe Asp Ile
1               5

<210> SEQ ID NO 71
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 71

Ala Arg Gly Arg Gly Ala Leu Thr Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 72

Ala Arg Lys Arg Asp Thr Phe Asp Ile
1               5

<210> SEQ ID NO 73
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 73

Ala Arg Lys Arg Asp Ala Phe Asp Ile
1               5

<210> SEQ ID NO 74
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence
```

```
<400> SEQUENCE: 74

Ala Arg Gly Arg Gly Ala Leu Thr Ala
1               5

<210> SEQ ID NO 75
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 75

Ala Arg Ser Arg Tyr Phe Asp Leu
1               5

<210> SEQ ID NO 76
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 76

Ala Arg Gln Lys Gly Met Asp Val
1               5

<210> SEQ ID NO 77
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 77

Ala Arg Lys Arg Gly Glu Phe Asp Tyr
1               5

<210> SEQ ID NO 78
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 78

Ala Arg Lys Arg Lys Tyr Phe Asp Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 79

Ala Arg Lys Arg Ser Ser Tyr Asp Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence
```

```
<400> SEQUENCE: 80

Ala Arg Ser Arg Tyr Phe Asp Leu
1               5

<210> SEQ ID NO 81
<211> LENGTH: 9
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 81

Ala Arg Lys Arg Gly Thr Phe Asp Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 82

Ala Arg Thr Arg Val Phe Asp Leu
1               5

<210> SEQ ID NO 83
<211> LENGTH: 13
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 83

Ala Arg Gly Gly Arg Asn Trp Ala Asp Ala Phe Asp Ile
1               5                   10

<210> SEQ ID NO 84
<211> LENGTH: 8
<212> TYPE: PRT
<213> ORGANISM: Artificial Sequence
<220> FEATURE:
<223> OTHER INFORMATION: Made in Lab - Synthesized VHCDR3 sequence

<400> SEQUENCE: 84

Ala Arg Ser Arg Tyr Phe Asp Tyr
1               5

<210> SEQ ID NO 85
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 85

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 86

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 87
<211> LENGTH: 108
<212> TYPE: PRT
<213> ORGANISM: Artificial Sequence
<220> FEATURE:
<223> OTHER INFORMATION: Made in Lab - synthesized VL sequence

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 88

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Ile Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 90

Asp Ile Gln Val Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Met Glu Ile Lys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Ser Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Thr Phe Gly Gln Gly Thr Lys Val Glu Ile Lys
            100                 105

<210> SEQ ID NO 92
<211> LENGTH: 106
<212> TYPE: PRT
<213> ORGANISM: Artificial Sequence
<220> FEATURE:
<223> OTHER INFORMATION: Made in Lab - synthesized VL sequence

<400> SEQUENCE: 92

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Val Glu Ile Lys
            100                 105

<210> SEQ ID NO 93
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Thr Phe Gly Gln Gly Thr Lys Val Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Thr Phe Gly Gln Gly Thr Lys Val Glu Ile Lys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 95

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Gly Ser Tyr
            20                  25                  30

Leu Ala Trp Cys Gln Gln Lys Pro Gly Lys Ala Pro Lys Leu Leu Ile
        35                  40                  45

Tyr Ala Ala Ser Thr Leu Gln Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 96
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 96

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Ile Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Thr Ser Tyr Pro Tyr
                85                  90                  95

Thr Phe Gly Gln Gly Thr Lys Leu Glu Ile Lys
            100                 105

<210> SEQ ID NO 97
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 97

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105

<210> SEQ ID NO 98
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 98

Asp Ile Gln Met Thr Gln Ser Pro Ser Ser Val Ser Ala Ser Glu Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Cys Asn Ser Ala Pro Phe
                85                  90                  95

Thr Phe Gly Pro Gly Thr Lys Val Asp Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 100

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Val Pro Arg Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys
            100                 105

<210> SEQ ID NO 101
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 101

Asp Ile Gln Met Thr Gln Ser Pro Ser Ala Met Ser Thr Ser Val Gly
1               5                   10                  15
Asp Arg Val Thr Ile Thr Cys Arg Ala Ser Gln Gly Ile Ser Asn Phe
            20                  25                  30
Leu Ala Trp Phe Gln Gln Lys Pro Gly Lys Val Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Tyr
                85                  90                  95
Thr Phe Gly Gln Gly Thr Lys Leu Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 102

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
Leu Ala Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Ala Asn Ser Phe Pro Leu
                85                  90                  95
Thr Phe Gly Gly Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 103

Asp Ile Gln Met Thr Gln Cys Pro Ser Ala Met Ser Ala Ser Val Gly
1               5                   10                  15

Asp Arg Val Ser Ile Thr Cys Arg Ala Ser Gln Gly Ile Ser Ile Tyr
            20                  25                  30

Leu Ala Trp Phe Gln Gln Lys Pro Gly Lys Val Pro Lys Arg Leu Val
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 104
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 104

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser His
                85                  90                  95

Thr Phe Gly Gln Gly Thr Lys Leu Glu Ile Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Made in Lab - synthesized VL sequence

<400> SEQUENCE: 105

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn His
            20                  25                  30

Leu Ala Trp Phe Gln Gln Lys Pro Gly Lys Val Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Glu Asp Phe Ala Thr Tyr Tyr Cys Leu Gln His Asn Ser Tyr Pro Tyr
            85                  90                  95

Thr Phe Gly Gln Gly Thr Lys Leu Glu Ile Lys
            100                 105

<210> SEQ ID NO 106
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 106

Gln Gly Ile Ser Ser Trp
1               5

<210> SEQ ID NO 107
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 107

Gln Ser Ile Ser Ser Trp
1               5

<210> SEQ ID NO 108
<211> LENGTH: 7
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 108

Gln Ser Val Ser Ser Phe
1               5

<210> SEQ ID NO 109
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 109

Gln Gly Ile Ser Ile Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 110

Gln Gly Ile Ser Asn Tyr
1               5

<210> SEQ ID NO 111
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence
```

```
<400> SEQUENCE: 111

Gln Gly Ile Ser Ser Tyr
1               5

<210> SEQ ID NO 112
<211> LENGTH: 7
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 112

Gln Ser Val Ser Ser Thr Tyr
1               5

<210> SEQ ID NO 113
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 113

Gln Ser Ile Ser Ser Trp
1               5

<210> SEQ ID NO 114
<211> LENGTH: 7
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 114

Gln Ser Val Ser Ser Tyr
1               5

<210> SEQ ID NO 115
<211> LENGTH: 7
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 115

Gln Ser Val Ser Ser Thr Tyr
1               5

<210> SEQ ID NO 116
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 116

Gln Asp Ile Gly Ser Tyr
1               5

<210> SEQ ID NO 117
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence
```

<400> SEQUENCE: 117

Gln Gly Ile Ser Ile Tyr
1               5

<210> SEQ ID NO 118
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 118

Gln Gly Ile Ser Asn Tyr
1               5

<210> SEQ ID NO 119
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 119

Gln Gly Ile Ser Arg Trp
1               5

<210> SEQ ID NO 120
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 120

Gln Gly Ile Ser Asn Tyr
1               5

<210> SEQ ID NO 121
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 121

Gln Gly Ile Ser Asn Tyr
1               5

<210> SEQ ID NO 122
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 122

Gln Gly Ile Ser Asn Phe
1               5

<210> SEQ ID NO 123
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

```
<400> SEQUENCE: 123

Gln Gly Ile Ser Ser Trp
1               5

<210> SEQ ID NO 124
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 124

Gln Gly Ile Ser Ile Tyr
1               5

<210> SEQ ID NO 125
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 125

Gln Ser Ile Ser Thr Trp
1               5

<210> SEQ ID NO 126
<211> LENGTH: 6
<212> TYPE: PRT
<213> ORGANISM: Artificial Sequence
<220> FEATURE:
<223> OTHER INFORMATION: Made in Lab - Synthesized VLCDR1 sequence

<400> SEQUENCE: 126

Gln Gly Ile Ser Asn His
1               5

<210> SEQ ID NO 127
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 127

Ala Ala Ser
1

<210> SEQ ID NO 128
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 128

Lys Ala Ser
1

<210> SEQ ID NO 129
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence
```

```
<400> SEQUENCE: 129

Gly Thr Ser
1

<210> SEQ ID NO 130
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 130

Ala Ala Ser
1

<210> SEQ ID NO 131
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 131

Ala Ala Ser
1

<210> SEQ ID NO 132
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 132

Ala Ala Ser
1

<210> SEQ ID NO 133
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 133

Gly Ala Ser
1

<210> SEQ ID NO 134
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 134

Lys Ala Ser
1

<210> SEQ ID NO 135
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence
```

```
<400> SEQUENCE: 135

Gly Ala Ser
1

<210> SEQ ID NO 136
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 136

Gly Ala Ser
1

<210> SEQ ID NO 137
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 137

Ala Ala Ser
1

<210> SEQ ID NO 138
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 138

Ala Ala Ser
1

<210> SEQ ID NO 139
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 139

Ala Ala Ser
1

<210> SEQ ID NO 140
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 140

Ala Ala Ser
1

<210> SEQ ID NO 141
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence
```

```
<400> SEQUENCE: 141

Ala Ala Ser
1

<210> SEQ ID NO 142
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 142

Ala Ala Ser
1

<210> SEQ ID NO 143
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 143

Ala Ala Ser
1

<210> SEQ ID NO 144
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 144

Ala Ala Ser
1

<210> SEQ ID NO 145
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 145

Gly Ala Ser
1

<210> SEQ ID NO 146
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence

<400> SEQUENCE: 146

Lys Ala Ser
1

<210> SEQ ID NO 147
<211> LENGTH: 3
<212> TYPE: PRT
<213> ORGANISM: Artificial Sequence
<220> FEATURE:
<223> OTHER INFORMATION: Made in Lab - Synthesized VLCDR2 sequence
```

```
<400> SEQUENCE: 147

Ala Ala Ser
1

<210> SEQ ID NO 148
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 148

Gln Gln Ala Asn Ser Phe Pro Arg Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 149

Gln Gln Tyr Asn Ser Tyr Ser Arg Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 150

Gln Gln Tyr Gly Ser Ser Pro Tyr Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 151

Leu Gln His Asn Ser Tyr Pro Leu Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 152

Gln Gln Tyr Asn Ser Tyr Pro Leu Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence
```

<400> SEQUENCE: 153

Gln Gln Leu Asn Ser Tyr Pro Leu Thr
1               5

<210> SEQ ID NO 154
<211> LENGTH: 8
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 154

Gln Gln Tyr Gly Ser Ser Arg Thr
1               5

<210> SEQ ID NO 155
<211> LENGTH: 8
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 155

Gln Gln Tyr Asn Ser Tyr Ser Thr
1               5

<210> SEQ ID NO 156
<211> LENGTH: 8
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 156

Gln Gln Tyr Gly Ser Ser Arg Thr
1               5

<210> SEQ ID NO 157
<211> LENGTH: 8
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 157

Gln Gln Tyr Gly Ser Ser Arg Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 158

Gln Gln Leu Asn Ser Tyr Pro Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

```
<400> SEQUENCE: 159

Leu Gln His Thr Ser Tyr Pro Tyr Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 160

Leu Gln His Asn Ser Tyr Pro Pro Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 161

Gln Gln Ala Asn Ser Phe Pro Leu Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 162

Gln Lys Cys Asn Ser Ala Pro Phe Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 163

Leu Gln His Asn Ser Tyr Pro Trp Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 164

Leu Gln His Asn Ser Tyr Pro Tyr Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence
```

<400> SEQUENCE: 165

Gln Gln Ala Asn Ser Phe Pro Leu Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 166

Leu Gln His Asn Ser Tyr Pro Leu Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 167

Gln Gln Tyr Asn Ser Tyr Ser His Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Made in Lab - Synthesized VLCDR3 sequence

<400> SEQUENCE: 168

Leu Gln His Asn Ser Tyr Pro Tyr Thr
1               5

<210> SEQ ID NO 169
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 169
caggtgcagc tgcaggagtc gggcccagga ctggtgaagc cttcggagac cctgtccctc      60
acctgcactg tctctggtgg ctccatcagt agttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agggaaggga     300
ggtactgact actggggcca gggaaccctg gtcaccgtct cctcag                    346

<210> SEQ ID NO 170
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 170

```
caggtgcagc tgcaggagtc gggcccagga ctggtgaagc cttcggagac cctgtccctc    60
acctgcactg tctctggtgg ctccatcaga acttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag aaagaagggt   300
gcttttgata tctggggcca aggacaatg gtcaccgtct cttcag                   346
```

<210> SEQ ID NO 171
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 171

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag aaaaagggga   300
ttagatatct ggggccaagg gacaatggtc accgtctctt cag                     343
```

<210> SEQ ID NO 172
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 172

```
caggtgcagc tgcaggagtc gggcccagga ctggtgaagg cttcggagac cctgtccctc    60
acctgcactg tctctggtgg ctccatcagt ggttactact ggagctggat ccggcagccc   120
gccgggaagg gactggagtg gattgggcgt atctataaca gtgggagcac caactacaac   180
ccctccctca agagtcgagt caccatgtca gtagacacgt ccaagaacca gttctccctg   240
aagctgagct ctgtgaccgc cgcggacacg gccgtgtatt actgtgcgag gcaaacttat   300
cttgactact ggggccaggg aaccctggtc accgtctcct cag                     343
```

<210> SEQ ID NO 173
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 173

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caattacaac   180
ccctccctca agagtcgagt caccatatca gtagacacgt ccaagaacca gttctccctg   240
```

```
aagctgaact ctgtgaccgc tgcggacacg gccgtgtatt actgtgcgag aaagagagct    300
tttcttgact actggggcca gggaaccctg gtcaccgtct cctcag                   346
```

<210> SEQ ID NO 174
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 174

```
caggtgcagc tgcaggagtc gggcccagga ctggtgaagc cttcggagac cctgtccctc     60
acctgcactg tctctggtgg ctccatcaat aattactact ggagctggat ccggcagccc    120
ccagggaagg gactggagtg gattgggtat atctattaca gtgggagcac caactaccac    180
ccctccctca agagtcgagt caccatatca gtggacacgt ccaagaacca gttctccctg    240
aagctgacct ctgtgaccgc tgcggacacg gccgtttttt actgtgcgag agggagacgt    300
gccctgactg cctggggcca gggaaccctg gtcaccgtct cctcag                   346
```

<210> SEQ ID NO 175
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 175

```
caggtgcagc tgcaggagtc gggcccagga ctggtgaagc cttcggagac cctgtccctc     60
acctgcactg tctctggtgg ctccatcagt acttactact ggagctggat ccggcagccc    120
ccagggaagg gactggagtg gattgggtat atctattaca gtgggaccac caactacaac    180
ccctccctca agagtcgagt caccatatca gtagacacgt ccaagaacca gttctccctg    240
aagctgagct ctgtgaccgc tgcggacacg gccgtatatt actgtgcgag aaagcgtgat    300
gcttttgata tctggggcca aggacaaatg gtcaccgtct cttcag                   346
```

<210> SEQ ID NO 176
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 176

```
caggtgcagc tgcaggagtc gggcccagga ctggtgaagc cttcggagac cctgtccctc     60
acctgcactg tctctggtgg ctccatcagt ttttactact ggacctggat ccggcagccc    120
ccaggtaagg gactggagtg gattggcttt atctattaca gtgggagcac caactacaac    180
ccctccctca agagtcgagt caccatatca gtagacacgt ccaagaacca gttctccctg    240
aagctgagct ctgtgaccgc tgcggacacg gccgtgtatt actgtgcgag aggaagaggt    300
gccctaactg cctggggcca gggaaccctg gtcaccgtct cctcag                   346
```

<210> SEQ ID NO 177
<211> LENGTH: 346
<212> TYPE: DNA
<213> ORGANISM: Artificial Sequence

```
<220> FEATURE:
<223> OTHER INFORMATION: Made in Lab - synthesized VH polynucleotide
      sequence

<400> SEQUENCE: 177
caggtgcagc tgcaggagtc gggcccagga ctggtgaagc cttcggagac cctgtccctc      60
acctgcactg tctctggtgg ctccatcagt aattactact ggagctggat ccggcagccc     120
cccgggaagg gactggagtg gattggatat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag aaagcgtgat     300
acttttgata tctggggcca aggacaatg gtcaccgtct cttcag                     346

<210> SEQ ID NO 178
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 178
caggtgcagc tgcaggggtc gggcccagga ctggtgaagc cttcggagac cctgtccctc      60
acctgcactg tctctggtgg ctccatcaat aattactact ggagctggat ccggcagccc     120
ccagggaagg gactggagtg gattgggtat atctattaca gtgggagcac caactccaac     180
ccctccctca agagtcgagt caccatatca gtagacacgt ccaagaacca gttctccctg     240
aagctgaact ctgtgaccgc tgcggacacg gccgtgtatt actgtgcgag aaagcgtgat     300
gcttttgata tctggggcca aggacaatg gtcaccgtct cttcag                     346

<210> SEQ ID NO 179
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 179
caggtgcagc tgcaggagtc gggcccagga ctgatgaagc cttcggagac cctgtccctc      60
acctgtactg tctctggtgg ctccatcagt agttactact ggacctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagctgagct ctgtgaccgc tgcggacacg gccgtgtatt actgtgcgag agggagaggt     300
gccctaactg cctggggcca gggaaccctg gtcaccgtct cctcag                    346

<210> SEQ ID NO 180
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 180
caggtgcagc tgcaggagtc gggcccagga ctggtgaagc cttcggagac cctgtccctc      60
acctgcactg tctctggtgg ctccatcagt aattactact ggagctggat ccggcagccc    120
```
ccagggaagg gactggagtg gattgggtat atctattaca gtgggagcac caactacaac    180
ccctccctca agagtcgagt caccatatca gtagacacgt ccaagaacca gttctccctg    240
aagctgagct ctgtgaccgc tgcggacacg gccgtgtatt actgtgcgag atcacggtac    300
ttcgatctct ggggccgtgg caccctggtc actgtctcct cag                      343

<210> SEQ ID NO 181
<211> LENGTH: 342
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 181
caggtgcagt tgcaggagtc gggcccagga ctggtgaagc cttcggagac cctgtccctc     60
acctgcactg tctctggtgg ctccatcaat aattactact ggagctggat ccggcagccc   120
ccagggaagg gactggagtg gattgggtat atctattaca gtgggagcac caactacaac   180
ccctccctca ggagtcgagt caccatatca gtagacacgt ccaagaacca gttctccctg   240
aagctgagct ctgtggccgc tgcggacacg gccgtgtatt actgtgcgag acaaaagggt   300
atggacgtct ggggccaagg gaccacggtc accgtctcct ca                      342

<210> SEQ ID NO 182
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 182
caggtgcagc tgcaggagtc gggcccagga ctggtgaagc cttcggagac cctgtccctc     60
acctgcactg tctctggtgg ctccatcagt agttactact ggagctggat ccggcagccc   120
ccagggaagg gactggagtg gattgggtat atctattaca gtgggaccac caactacaac   180
ccctccctca agagtcgagt caccatatca gtagacacgt ccaagaacca gttctccctg   240
aagctgagct ctgtgaccgc tgcggacacg gccgtgtatt actgtgcgag aaagagggga   300
gagtttgact actggggcca gggaaccctg gtcaccgtct cctcaa                   346

<210> SEQ ID NO 183
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 183
caggtgcagc tgcaggagtc gggcccagga ctggtgaagc cttcggagac cctgtccctc     60
acctgcactg tctctggtgg ctccatcagt agttactact ggagctggat ccggcagccc   120
ccagggaagg gactggagtg gattgggtat atctattaca gtgggagcac caactacaac   180
ccgtccctca agagtcgagt caccatatca gtagacacgt ccaagaacca gttctccctg   240
aagctgagct ctgtgaccgc tgcggacacg gccgtgtatt actgtgcgag aaagcggaag   300
tactttgact actggggcca gggaaccctg gtcaccgtct cctcag                   346

<210> SEQ ID NO 184

```
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 184
caggtgcagc tgcaggagtc gggcccagga ctggtgaagc cttcggagac cctgtccctc     60
acctgcactg tctctggtgg ctccatcaat tattactact ggagctggat ccggcagccc    120
ccagggaagg gactggagtg gattgggtat atctattaca gtgggagcac caactacaat    180
ccctccctca agagtcgagt caccatatca gtagacacgt ccaagaacca gttctccctg    240
aagttgagtt ctgtgaccgc tgcggacacg gccgtgtatt actgtgcgag aaagcgcagc    300
tcctatgact actggggcca gggaaccctg gtcaccgtct cctcag                   346

<210> SEQ ID NO 185
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 185
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagaacca gttctccctg    240
aagctgagct ctgtgaccgc tgcggacacg gccgtctatt actgtgcgag atcacggtac    300
ttcgatctct ggggccgtgg caccctggtc actgtctcct cag                      343

<210> SEQ ID NO 186
<211> LENGTH: 346
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 186
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattggatat gtctattaca gtgggggcac caactacaac    180
ccctccctca agagtcgagt caccatatcc gtagacacgt ccaagaacca gttctccctg    240
aaactgagtt ctgtgaccgc tgcggacacg gccgtgtatt actgtgcgag aaagagggga    300 accttttgact actggggcca gggaaccctg gtcaccgtct cctcag                  346

<210> SEQ ID NO 187
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence
```

<400> SEQUENCE: 187

```
caggtgcagc tgcaggagtc gggcccagga ctggtgaagc cctcggagac cctgtccctc    60
acctgcactg tctctggtgg ctccatcagt agttactact ggagctggat ccggcagccc   120
ccagggaagg gactggagtg gattgggtat gtctattaca gtgggagcac caactacaac   180
ccctccctca agagtcgagt caccatatca gtggacacgt ccaagaacca gttctccctg   240
aagctgagct ctgtgaccgc tgcggacacg gccgtgtatt actgtgcgag aactcgagtg   300
ttcgatctct ggggccgtgg caccctggtc actgtctcct cag                     343
```

<210> SEQ ID NO 188
<211> LENGTH: 361
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 188

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccctaacagtggtgg cacaaactat    180
gcacagaagt ttcagggcag ggtcaccatg accagggaca cgtccatcag cacagcctac   240
atggagctga gcaggctgag atctgacgac acggccgtgt attactgtgc gagggggt    300
cggaactggg ccgatgcttt tgatatctgg ggccaaggga caatggtcac cgtctcttca   360
g                                                                    361
```

<210> SEQ ID NO 189
<211> LENGTH: 343
<212> TYPE: DNA
<213> ORGANISM: Artificial Sequence
<220> FEATURE:
<223> OTHER INFORMATION: Made in Lab - synthesized VH polynucleotide
      sequence

<400> SEQUENCE: 189

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag atctcggtac   300
tttgactact ggggccaggg aaccctggtc accgtctcct cag                     343
```

<210> SEQ ID NO 190
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 190

```
ggtggctcca tcagtagtta ctac                                           24
```

<210> SEQ ID NO 191
<211> LENGTH: 24

```
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 191
ggtggctcca tcagaactta ctac                                              24

<210> SEQ ID NO 192
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 192
ggtggctcca tcagtagtta ctac                                              24

<210> SEQ ID NO 193
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 193
ggtggctcca tcagtggtta ctac                                              24

<210> SEQ ID NO 194
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 194
ggtggctcca tcagtagtta ctac                                              24

<210> SEQ ID NO 195
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 195
ggtggctcca tcaataatta ctac                                              24

<210> SEQ ID NO 196
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 196
ggtggctcca tcagtactta ctac                                              24

<210> SEQ ID NO 197
<211> LENGTH: 24
<212> TYPE: DNA
```

```
<213> ORGANISM: Artificial Sequence
<220> FEATURE:
<223> OTHER INFORMATION: Made in Lab - Synthesized VHCDR1 polynucleotide
      sequence

<400> SEQUENCE: 197
ggtggctcca tcagttttta ctac                                          24

<210> SEQ ID NO 198
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 198
ggtggctcca tcagtaatta ctac                                          24

<210> SEQ ID NO 199
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 199
ggtggctcca tcaataatta ctac                                          24

<210> SEQ ID NO 200
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 200
ggtggctcca tcagtagtta ctac                                          24

<210> SEQ ID NO 201
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 201
ggtggctcca tcagtaatta ctac                                          24

<210> SEQ ID NO 202
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 202
ggtggctcca tcaataatta ctac                                          24

<210> SEQ ID NO 203
<211> LENGTH: 24
<212> TYPE: DNA
<213> ORGANISM: Artificial Sequence
```

<220> FEATURE:
<223> OTHER INFORMATION: Made in Lab - Synthesized VHCDR1 polynucleotide
      sequence

<400> SEQUENCE: 203
ggtggctcca tcagtagtta ctac                                              24

<210> SEQ ID NO 204
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 204
ggtggctcca tcagtagtta ctac                                              24

<210> SEQ ID NO 205
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 205
ggtggctcca tcaattatta ctac                                              24

<210> SEQ ID NO 206
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 206
ggtggctcca tcagtagtta ctac                                              24

<210> SEQ ID NO 207
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 207
ggtggctcca tcagtagtta ctac                                              24

<210> SEQ ID NO 208
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 208
ggtggctcca tcagtagtta ctac                                              24

<210> SEQ ID NO 209
<211> LENGTH: 24
<212> TYPE: DNA
<213> ORGANISM: Artificial Sequence
<220> FEATURE:

```
<223> OTHER INFORMATION: Made in Lab - Synthesized VHCDR1 polynucleotide
      sequence

<400> SEQUENCE: 209
ggatacacct tcaccggcta ctat                                            24

<210> SEQ ID NO 210
<211> LENGTH: 24
<212> TYPE: DNA
<213> ORGANISM: Artificial Sequence
<220> FEATURE:
<223> OTHER INFORMATION: Made in Lab - Synthesized VHCDR1 polynucleotide
      sequence

<400> SEQUENCE: 210
ggtggctcca tcagtagtta ctac                                            24

<210> SEQ ID NO 211
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 211
atctattaca gtgggagcac c                                               21

<210> SEQ ID NO 212
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 212
atctattaca gtgggagcac c                                               21

<210> SEQ ID NO 213
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 213
atctattaca gtgggagcac c                                               21

<210> SEQ ID NO 214
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 214
atctataaca gtgggagcac c                                               21

<210> SEQ ID NO 215
<211> LENGTH: 21
<212> TYPE: DNA
<213> ORGANISM: Artificial Sequence
<220> FEATURE:
```

```
<223> OTHER INFORMATION: Made in Lab - Synthesized VHCDR2 polynucleotide
      sequence

<400> SEQUENCE: 215
atctattaca gtgggagcac c                                              21

<210> SEQ ID NO 216
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 216
atctattaca gtgggagcac c                                              21

<210> SEQ ID NO 217
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 217
atctattaca gtgggaccac c                                              21

<210> SEQ ID NO 218
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 218
atctattaca gtgggagcac c                                              21

<210> SEQ ID NO 219
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 219
atctattaca gtgggagcac c                                              21

<210> SEQ ID NO 220
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 220
atctattaca gtgggagcac c                                              21

<210> SEQ ID NO 221
<211> LENGTH: 21
<212> TYPE: DNA
<213> ORGANISM: Artificial Sequence
```

```
<220> FEATURE:
<223> OTHER INFORMATION: Made in Lab - Synthesized VHCDR2 polynucleotide
      sequence

<400> SEQUENCE: 221
atctattaca gtgggagcac c                                              21

<210> SEQ ID NO 222
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 222
atctattaca gtgggagcac c                                              21

<210> SEQ ID NO 223
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 223
atctattaca gtgggagcac c                                              21

<210> SEQ ID NO 224
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 224
atctattaca gtgggaccac c                                              21

<210> SEQ ID NO 225
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 225
atctattaca gtgggagcac c                                              21

<210> SEQ ID NO 226
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 226
atctattaca gtgggagcac c                                              21

<210> SEQ ID NO 227
<211> LENGTH: 21
<212> TYPE: DNA
<213> ORGANISM: Artificial Sequence
<220> FEATURE:
```

```
<223> OTHER INFORMATION: Made in Lab - Synthesized VHCDR2 polynucleotide
      sequence

<400> SEQUENCE: 227
atctattaca gtgggagcac c                                              21

<210> SEQ ID NO 228
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 228
gtctattaca gtgggggcac c                                              21

<210> SEQ ID NO 229
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 229
gtctattaca gtgggagcac c                                              21

<210> SEQ ID NO 230
<211> LENGTH: 24
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 230
atcaacccta acagtggtgg caca                                           24

<210> SEQ ID NO 231
<211> LENGTH: 21
<212> TYPE: DNA
<213> ORGANISM: Artificial Sequence
<220> FEATURE:
<223> OTHER INFORMATION: Made in Lab - Synthesized VHCDR2 polynucleotide
      sequence

<400> SEQUENCE: 231
atctattaca gtgggagcac c                                              21

<210> SEQ ID NO 232
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 232
gcgagaggga agggaggtac tgactac                                        27

<210> SEQ ID NO 233
<211> LENGTH: 27
<212> TYPE: DNA
<213> ORGANISM: Artificial Sequence
```

<220> FEATURE:
<223> OTHER INFORMATION: Made in Lab - Synthesized VHCDR3 polynucleotide
      sequence

<400> SEQUENCE: 233
gcgagaaaga agggtgcttt tgatatc                                        27

<210> SEQ ID NO 234
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 234
gcgagaaaaa ggggattaga tatc                                           24

<210> SEQ ID NO 235
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 235
gcgaggcaaa cttatcttga ctac                                           24

<210> SEQ ID NO 236
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 236
gcgagaaaga gagcttttct tgactac                                        27

<210> SEQ ID NO 237
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 237
gcgagaggga gacgtgccct gactgcc                                        27

<210> SEQ ID NO 238
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 238
gcgagaaagc gtgatgcttt tgatatc                                        27

<210> SEQ ID NO 239
<211> LENGTH: 27
<212> TYPE: DNA
<213> ORGANISM: Artificial Sequence
<220> FEATURE:

```
<223> OTHER INFORMATION: Made in Lab - Synthesized VHCDR3 polynucleotide
      sequence

<400> SEQUENCE: 239
gcgagaggaa gaggtgccct aactgcc                                       27

<210> SEQ ID NO 240
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 240
gcgagaaagc gtgatacttt tgatatc                                       27

<210> SEQ ID NO 241
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 241
gcgagaaagc gtgatgcttt tgatatc                                       27

<210> SEQ ID NO 242
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 242
gcgagaggga gaggtgccct aactgcc                                       27

<210> SEQ ID NO 243
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 243
gcgagatcac ggtacttcga tctc                                          24

<210> SEQ ID NO 244
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 244
gcgagacaaa agggtatgga cgtc                                          24

<210> SEQ ID NO 245
<211> LENGTH: 27
<212> TYPE: DNA
<213> ORGANISM: Artificial Sequence
```

```
<220> FEATURE:
<223> OTHER INFORMATION: Made in Lab - Synthesized VHCDR3 polynucleotide
      sequence

<400> SEQUENCE: 245
gcgagaaaga ggggagagtt tgactac                                           27

<210> SEQ ID NO 246
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 246
gcgagaaagc ggaagtactt tgactac                                           27

<210> SEQ ID NO 247
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 247
gcgagaaagc gcagctccta tgactac                                           27

<210> SEQ ID NO 248
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 248
gcgagatcac ggtacttcga tctc                                              24

<210> SEQ ID NO 249
<211> LENGTH: 27
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 249
gcgagaaaga ggggaaacctt tgactac                                          27

<210> SEQ ID NO 250
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 250
gcgagaactc gagtgttcga tctc                                              24

<210> SEQ ID NO 251
<211> LENGTH: 39
<212> TYPE: DNA
<213> ORGANISM: Artificial Sequence
<220> FEATURE:
```

```
<223> OTHER INFORMATION: Made in Lab - Synthesized VHCDR3 polynucleotide
      sequence

<400> SEQUENCE: 251
gcgagagggg gtcggaactg ggccgatgct tttgatatc                              39

<210> SEQ ID NO 252
<211> LENGTH: 24
<212> TYPE: DNA
<213> ORGANISM: Artificial Sequence
<220> FEATURE:
<223> OTHER INFORMATION: Made in Lab - Synthesized VHCDR3 polynucleotide
      sequence

<400> SEQUENCE: 252
gcgagatctc ggtactttga ctac                                             24

<210> SEQ ID NO 253
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 253
gacatccaga tgacccagtc tccatcttcc gtgtctgcat ctgtaggaga cagagtcacc       60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt ccctcggac  gttcggccaa     300 gggaccaagg tggaaatcaa ac                                              322

<210> SEQ ID NO 254
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 254
gacatccaga tgacccagtc tccttccacc ctgtctgcat ctgtaggaga cagagtcacc       60
atcacttgcc gggccagtca gagtattagt agctggttgg cctggtatca gcagaaacca     120
gggaaagccc ctaaggtcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attctcggac gttcggccaa     300
gggaccaagg tggaaatcaa ac                                              322

<210> SEQ ID NO 255
<211> LENGTH: 325
<212> TYPE: DNA
<213> ORGANISM: Artificial Sequence
<220> FEATURE:
<223> OTHER INFORMATION: Made in Lab - synthesized VL polynucleotide
      sequence
```

<400> SEQUENCE: 255

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gagtgttagc | agcagcttct | tagcctggta | ccagcagaaa | 120 |
| cctggccagg | ctcccaggct | cctcatctat | ggtacatcca | gcagggccac | tggcatccca | 180 |
| gacaggttca | gtggcagtgg | gtctgggaca | gacttcactc | tcaccatcag | cagactggag | 240 |
| cctgaagatt | ttgcagtgta | ttactgtcag | cagtatggta | gctcaccgta | cacttttggc | 300 |
| caggggacca | agctggagat | caaac | | | | 325 |

<210> SEQ ID NO 256
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 256

| | | | | | |
|---|---|---|---|---|---|
| gacatccaga | tgacccagtc | tccatctgcc | atgtctgcat | ctgtaggaga | cagagtcacc | 60 |
| atcacttgtc | gggcgagtca | gggcattagt | atttatttag | cctggtttca | gcagaaacca | 120 |
| gggaaagtcc | ctaagcgcct | gatctatgct | gcatccagtt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtctacag | cataatagtt | accctctcac | tttcggcgga | 300 |
| gggaccaagg | tggagatcaa | ac | | | | 322 |

<210> SEQ ID NO 257
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 257

| | | | | | |
|---|---|---|---|---|---|
| gacatccaga | tgacccagtc | tccatcctca | ctgtctgcat | ctgtaggaga | cagagtcacc | 60 |
| atcacttgtc | gggcgagtca | gggcattagc | aattatttag | cctggtttca | gcagaaacca | 120 |
| gggaaagccc | ctaagtccct | gatctatgct | gcatccagtt | tgcaaggtgg | ggtcccatca | 180 |
| aagttcagcg | gcagtggatc | tgggacagat | ttcactctca | ccatcagcag | cctgcagcct | 240 |
| gaagattttg | caacttatta | ctgccaacag | tataatagtt | accctctcac | tttcggcgga | 300 |
| gggaccaagg | tggagatcaa | ac | | | | 322 |

<210> SEQ ID NO 258
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 258

| | | | | | |
|---|---|---|---|---|---|
| gacatccagg | tgacccagtc | tccatccttc | ctgtctgcat | ctgtaggaga | cagagtcacc | 60 |
| atcacttgcc | gggccagtca | gggcattagc | agttatttag | cctggtatca | gcaaaaacca | 120 |
| gggaaagccc | ctaagctcct | gatctatgct | gcatccactc | tgcaaagtgg | ggtcccatca | 180 |
| aggttcagcg | gcagtggatc | tgggacagaa | ttcactctca | caatcagcag | cctgcagcct | 240 |

```
gaagattttg caacttatta ctgtcaacag cttaatagtt acccgctcac tttcggcgga    300
gggaccaaga tggagatcaa ac                                             322
```

<210> SEQ ID NO 259
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 259

```
gaaattgtgt tgacgcagtc tccaggcacc ctgtctttgt ctccagggga aagagccacc    60
ctctcctgca gggccagtca gagtgtcagc agcaccctact tagcctggtc ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gttcacggac gttcggccaa   300
gggaccaagg tggaaatcaa ac                                             322
```

<210> SEQ ID NO 260
<211> LENGTH: 319
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 260

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attcgacgtt cggccaaggg   300
accaaggtgg aaatcaagc                                                 319
```

<210> SEQ ID NO 261
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 261

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacggac gttcggccaa   300
gggaccaagg tggaaatcaa ac                                             322
```

<210> SEQ ID NO 262
<211> LENGTH: 322
<212> TYPE: DNA
<213> ORGANISM: Artificial Sequence

```
<220> FEATURE:
<223> OTHER INFORMATION: Made in Lab - synthesized VL polynucleotide
      sequence

<400> SEQUENCE: 262
gaaattgtgt tgacgcagtc tccaggcacc ctgtctttgt ctccagggga aagagccacc    60
ctctcctgca gggccagtca gagtgttagc agcacctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacggac gttcggccaa   300
gggaccaagg tggaaatcaa ac                                            322

<210> SEQ ID NO 263
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 263
gacatccagt tgacccagtc tccatccttc ctgtctgcat ctgtaggaga cagagtcacc    60
atcacttgcc gggccagtca ggacattggc agttatttag cctggtgtca gcaaaaacca   120
gggaaagccc ctaagctcct gatctatgct gcatccactt gcaaggtggg gtcccatca    180 aggttcagcg gcagtggatc tgggacagaa ttcactctca caatcagcag cctgcagcct   240
gaagattttg caacttatta ctgtcaacag cttaatagtt acccgctcac tttcggcgga   300
gggaccaagg tggagatcaa ac                                            322

<210> SEQ ID NO 264
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 264
gacatccaga tgacccagtc tccatctgcc atgtctgcat ctgtaggaga cagagtcacc    60
atcacttgtc gggcgagtca gggcattagc atttatttag cctggtttca gcagaaacca   120
gggaaagtcc ctaagcgcct gatctatgca gcttccagtt tgcaaagtgg ggtcccatca   180
aggttcagcg gcagtgggtc tgggacagaa ttcactctca caatcagcag cctgcagcct   240
gaagactttg caacttatta ctgtctacag cataccagtt acccgtacac ttttggccag   300
gggaccaagc tggagatcaa ac                                            322

<210> SEQ ID NO 265
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 265
gacatccaga tgacccagtc tccatctgcc atgtctgcat ctgtaggaga cagagtcacc    60
atcacttgtc gggcgagtca gggcattagc aattatttag cctggtttca gcagaaacca   120
```

```
gggaaagtcc ctaagcgcct gatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt accctccgac gttcggccaa      300
gggaccaagg tggaaatcaa ac                                               322
```

<210> SEQ ID NO 266
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 266

```
gacatccaga tgacccagtc tccatcttcc gtgtctgcat ctgaaggaga cagagtcacc       60
atcacttgtc gggcgagtca gggtattagc agatggttag cctggtatca gcagaaacca      120
gggaaagccc ctaagctcct gatctatgct gcatccagtt tgcaaagtgg ggtcccatca      180
aggttcagcg gcagtggatc tgggacagat ttcactctca ccatcagcag cctgcagcct      240
gaagattttg caacttacta ttgtcaacag gctaacagtt ccctctcac tttcggcgga      300 gggaccaagg tggagatcaa ac                                               322
```

<210> SEQ ID NO 267
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 267

```
gacatccaga tgacccagtc tccatcctcc ctgtctgcat ctgtaggaga cagagtcacc       60
atcacttgcc gggcgagtca gggcattagc aattatttag cctggtatca gcagaaacca      120
gggaaagttc ctaagctcct gatctatgct gcatccactt tgcaatcagg ggtcccatct      180
cggttcagtg gcagtggatc tgggacagat ttcactctca ccatcagcag cctgcagcct      240
gaagatgttg caacttatta ctgtcaaaag tgtaacagtg ccccattcac tttcggccct      300
gggaccaaag tggatatcaa ac                                               322
```

<210> SEQ ID NO 268
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 268

```
gacatccaga tgacccagtc tccatctgcc atgtctgcat ctgtaggaga cagagtcacc       60
atcacttgtc gggcgagtca gggcattagc aattatttag cctggtttca gcagaaacca      120
gggaaagtcc ctaggcgcct tatctatgct gcatccagtt tgcaaagtgg ggtcccatca      180
aggttcagcg gcagtggatc tgggacagaa ttcactctca caatcagcag cctgcagcct      240
gaagattttg caacttatta ctgtctacag cataatagtt acccgtggac gttcggccaa      300
gggaccaagg tggaaatcaa ac                                               322
```

<210> SEQ ID NO 269

<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 269

| gacatccaga tgacccagtc tccatctgcc atgtctacat ctgtaggaga cagagtcacc | 60 |
| atcacttgtc gggcgagtca gggcattagc aatttttag cctggtttca gcagaaacca | 120 |
| gggaaagtcc ctaagcgcct gatctatgct gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt acccgtacac ttttggccag | 300 |
| gggaccaagc tggagatcaa ac | 322 |

<210> SEQ ID NO 270
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 270

| gacatccaga tgacccagtc tccatcttcc gtgtctgcat ctgtaggaga cagagtcacc | 60 |
| atcacttgtc gggcgagtca gggtattagc agctggttag cctggtatca gcagaaacca | 120 |
| gggaaagccc ctaaactcct gatctatgct gcatccagtt tgcaaagtgg ggtcccatca | 180 |
| aggttcagcg gcagtggatc tgggacagat ttcactctca ccatcagcag cctgcagcct | 240 |
| gaagattttg caacttactt ttgtcaacag gctaacagtt ccctctcac tttcggcgga | 300 |
| gggaccaagg tggagatcaa ac | 322 |

<210> SEQ ID NO 271
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 271

| gacatccaga tgacccagtg tccatctgcc atgtctgcat ctgttggaga cagagtctcc | 60 |
| atcacttgtc gggcgagtca gggcattagc atttatttag cctggtttca gcagaaacca | 120 |
| gggaaagtcc ctaagcgcct ggtctatggt gcatccagtt tgcaaagtgg ggtcccatca | 180 |
| aggttcagcg gcagtggatc tgggacagaa ttcactctca caatcagcag cctgcagcct | 240 |
| gaagattttg caacttatta ctgtctacaa cataatagtt acccgctcac tttcggcgga | 300 |
| gggaccaagg tggagatcaa ac | 322 |

<210> SEQ ID NO 272
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 272

```
gacatccaga tgacccagtc tccttccacc ctgtctgcat ctgtaggaga cagagtcacc      60
atcacttgcc gggccagtca gagtattagt acctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attcgcatac ttttggccag     300
gggaccaagc tggagatcaa ac                                              322
```

<210> SEQ ID NO 273
<211> LENGTH: 322
<212> TYPE: DNA
<213> ORGANISM: Artificial Sequence
<220> FEATURE:
<223> OTHER INFORMATION: Made in Lab - synthesized VL polynucleotide
      sequence

<400> SEQUENCE: 273

```
gacatccaga tgacccagtc tccatctgcc atgtctgcat ctgtaggaga cagagtcacc      60
atcacttgtc gggcgagtca gggcattagc aatcatttag cctggtttca gcagaaacca     120
gggaaagtcc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataatagtt acccgtacac ttttggccag     300
gggaccaagc tggagatcaa ac                                              322
```

<210> SEQ ID NO 274
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 274

```
cagggtatta gcagctgg                                                    18
```

<210> SEQ ID NO 275
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 275

```
cagagtatta gtagctgg                                                    18
```

<210> SEQ ID NO 276
<211> LENGTH: 21
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 276

```
cagagtgtta gcagcagctt c                                                21
```

<210> SEQ ID NO 277

```
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 277
cagggcatta gtatttat                                                       18

<210> SEQ ID NO 278
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 278
cagggcatta gcaattat                                                       18

<210> SEQ ID NO 279
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 279
cagggcatta gcagttat                                                       18

<210> SEQ ID NO 280
<211> LENGTH: 21
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 280
cagagtgtca gcagcaccta c                                                   21

<210> SEQ ID NO 281
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 281
cagagtatta gtagctgg                                                       18

<210> SEQ ID NO 282
<211> LENGTH: 21
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 282
cagagtgtta gcagcagcta c                                                   21

<210> SEQ ID NO 283
<211> LENGTH: 21
```

```
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 283
cagagtgtta gcagcaccta c                                          21

<210> SEQ ID NO 284
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 284
caggacattg gcagttat                                              18

<210> SEQ ID NO 285
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 285
cagggcatta gcatttat                                              18

<210> SEQ ID NO 286
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 286
cagggcatta gcaattat                                              18

<210> SEQ ID NO 287
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 287
cagggtatta gcagatgg                                              18

<210> SEQ ID NO 288
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 288
cagggcatta gcaattat                                              18

<210> SEQ ID NO 289
<211> LENGTH: 18
<212> TYPE: DNA
```

<213> ORGANISM: Artificial Sequence
<220> FEATURE:
<223> OTHER INFORMATION: Made in Lab - Synthesized VLCDR1 polynucleotid
      sequence

<400> SEQUENCE: 289
cagggcatta gcaattat                                                 18

<210> SEQ ID NO 290
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 290
cagggcatta gcaatttt                                                 18

<210> SEQ ID NO 291
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 291
cagggtatta gcagctgg                                                 18

<210> SEQ ID NO 292
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 292
cagggcatta gcatttat                                                 18

<210> SEQ ID NO 293
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 293
cagagtatta gtacctgg                                                 18

<210> SEQ ID NO 294
<211> LENGTH: 18
<212> TYPE: DNA
<213> ORGANISM: Artificial Sequence
<220> FEATURE:
<223> OTHER INFORMATION: Made in Lab - Synthesized VLCDR1 polynucleotid
      sequence

<400> SEQUENCE: 294
cagggcatta gcaatcat                                                 18

<210> SEQ ID NO 295
<211> LENGTH: 9
<212> TYPE: DNA
<213> ORGANISM: Artificial Sequence

```
<220> FEATURE:
<223> OTHER INFORMATION: Made in Lab - Synthesized VLCDR2 polynucleotide
      sequence

<400> SEQUENCE: 295 gctgcatcc                                                                 9

<210> SEQ ID NO 296
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 296 aaggcgtct                                                                 9

<210> SEQ ID NO 297
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 297 ggtacatcc                                                                 9

<210> SEQ ID NO 298
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 298 gctgcatcc                                                                 9

<210> SEQ ID NO 299
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 299 gctgcatcc                                                                 9

<210> SEQ ID NO 300
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 300 gctgcatcc                                                                 9

<210> SEQ ID NO 301
<211> LENGTH: 9
<212> TYPE: DNA
<213> ORGANISM: Artificial Sequence
<220> FEATURE:
```

<223> OTHER INFORMATION: Made in Lab - Synthesized VLCDR2 polynucleotide
      sequence

<400> SEQUENCE: 301 ggtgcatcc                                                                      9

<210> SEQ ID NO 302
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 302 aaggcgtct                                                                      9

<210> SEQ ID NO 303
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 303 ggtgcatcc                                                                      9

<210> SEQ ID NO 304
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 304 ggtgcatcc                                                                      9

<210> SEQ ID NO 305
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 305 gctgcatcc                                                                      9

<210> SEQ ID NO 306
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 306 gcagcttcc                                                                      9

<210> SEQ ID NO 307
<211> LENGTH: 9
<212> TYPE: DNA
<213> ORGANISM: Artificial Sequence

```
<220> FEATURE:
<223> OTHER INFORMATION: Made in Lab - Synthesized VLCDR2 polynucleotide
      sequence

<400> SEQUENCE: 307 gctgcatcc                                                                    9

<210> SEQ ID NO 308
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 308 gctgcatcc                                                                    9

<210> SEQ ID NO 309
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 309 gctgcatcc                                                                    9

<210> SEQ ID NO 310
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 310 gctgcatcc                                                                    9

<210> SEQ ID NO 311
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 311 gctgcatcc                                                                    9

<210> SEQ ID NO 312
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 312 gctgcatcc                                                                    9

<210> SEQ ID NO 313
<211> LENGTH: 9
<212> TYPE: DNA
<213> ORGANISM: Artificial Sequence
<220> FEATURE:
```

```
<223> OTHER INFORMATION: Made in Lab - Synthesized VLCDR2 polynucleotide
      sequence

<400> SEQUENCE: 313 ggtgcatcc                                                                  9

<210> SEQ ID NO 314
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 314 aaggcgtct                                                                  9

<210> SEQ ID NO 315
<211> LENGTH: 9
<212> TYPE: DNA
<213> ORGANISM: Artificial Sequence
<220> FEATURE:
<223> OTHER INFORMATION: Made in Lab - Synthesized VLCDR2 polynucleotide
      sequence

<400> SEQUENCE: 315 gctgcatcc                                                                  9

<210> SEQ ID NO 316
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 316
caacaggcta acagtttccc tcggacg                                             27

<210> SEQ ID NO 317
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 317
caacagtata atagttattc tcggacg                                             27

<210> SEQ ID NO 318
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 318
cagcagtatg gtagctcacc gtacact                                             27

<210> SEQ ID NO 319
<211> LENGTH: 27
<212> TYPE: DNA
<213> ORGANISM: Artificial Sequence
```

```
<220> FEATURE:
<223> OTHER INFORMATION: Made in Lab - Synthesized VLCDR3 polynucleotide
      sequence

<400> SEQUENCE: 319
ctacagcata atagttaccc tctcact                                              27

<210> SEQ ID NO 320
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 320
caacagtata atagttaccc tctcact                                              27

<210> SEQ ID NO 321
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 321
caacagctta atagttaccc gctcact                                              27

<210> SEQ ID NO 322
<211> LENGTH: 24
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 322
cagcagtatg gtagttcacg gacg                                                 24

<210> SEQ ID NO 323
<211> LENGTH: 24
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 323
caacagtata atagttattc gacg                                                 24

<210> SEQ ID NO 324
<211> LENGTH: 24
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 324
cagcagtatg gtagctcacg gacg                                                 24

<210> SEQ ID NO 325
<211> LENGTH: 24
<212> TYPE: DNA
<213> ORGANISM: Artificial Sequence
<220> FEATURE:
```

<223> OTHER INFORMATION: Made in Lab - Synthesized VLCDR3 polynucleotide
      sequence

<400> SEQUENCE: 325
cagcagtatg gtagctcacg gacg                                          24

<210> SEQ ID NO 326
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 326
caacagctta atagttaccc gctcact                                       27

<210> SEQ ID NO 327
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 327
ctacagcata ccagttaccc gtacact                                       27

<210> SEQ ID NO 328
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 328
ctacagcata atagttaccc tccgacg                                       27

<210> SEQ ID NO 329
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 329
caacaggcta acagtttccc tctcact                                       27

<210> SEQ ID NO 330
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 330
caaaagtgta acagtgcccc attcact                                       27

<210> SEQ ID NO 331
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 331
ctacagcata atagttaccc gtggacg                                         27

<210> SEQ ID NO 332
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 332
ctacagcata atagttaccc gtacact                                         27

<210> SEQ ID NO 333
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 333
caacaggcta acagtttccc tctcact                                         27

<210> SEQ ID NO 334
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 334
ctacaacata atagttaccc gctcact                                         27

<210> SEQ ID NO 335
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 335
caacagtata atagttattc gcatact                                         27

<210> SEQ ID NO 336
<211> LENGTH: 27
<212> TYPE: DNA
<213> ORGANISM: Artificial Sequence
<220> FEATURE:
<223> OTHER INFORMATION: Made in Lab - Synthesized VLCDR3 polynucleotide
      sequence

<400> SEQUENCE: 336
ctacagcata atagttaccc gtacact                                         27

<210> SEQ ID NO 337
<211> LENGTH: 24
<212> TYPE: DNA
<213> ORGANISM: Artificial Sequence
<220> FEATURE:

```
<223> OTHER INFORMATION: Primer

<400> SEQUENCE: 337
ggttcgggga agtagtcctt gacc                                      24

<210> SEQ ID NO 338
<211> LENGTH: 22
<212> TYPE: DNA
<213> ORGANISM: Artificial Sequence
<220> FEATURE:
<223> OTHER INFORMATION: Primer

<400> SEQUENCE: 338
ccgattggag ggcgttatcc ac                                        22
```

UNITED STATES PATENT AND TRADEMARK OFFICE
CERTIFICATE OF CORRECTION

| | | |
|---|---|---|
| PATENT NO. | : 11,352,425 B2 | Page 1 of 1 |
| APPLICATION NO. | : 16/347926 | |
| DATED | : June 7, 2022 | |
| INVENTOR(S) | : Lippincott et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Tenth Day of June, 2025

Coke Morgan Stewart
*Acting Director of the United States Patent and Trademark Office*